(12) United States Patent
O'Brien-Simpson et al.

(10) Patent No.: US 6,962,706 B1
(45) Date of Patent: Nov. 8, 2005

(54) **SYNTHETIC PEPTIDES CONTAINING PROTECTIVE EPITOPES FOR THE TREATMENT AND PREVENTION OF PERIODONTITIS ASSOCIATED WITH *PORPHYROMONAS GINGIVALIS***

(75) Inventors: Neil Martin O'Brien-Simpson, Brunswick (AU); Eric Charles Reynolds, North Balwyn (AU)

(73) Assignees: The University of Melbourne, Parkville (AU); CSL Limited, Parkville (AU); Victorian Dairy Industry Association, Abbotsford (AU)

( * ) Notice: Subject to any disclaimer, the term of this patent is extended or adjusted under 35 U.S.C. 154(b) by 0 days.

(21) Appl. No.: 09/914,612

(22) PCT Filed: Mar. 1, 2000

(86) PCT No.: PCT/AU00/00142

§ 371 (c)(1),
(2), (4) Date: Jan. 11, 2002

(87) PCT Pub. No.: WO00/52041

PCT Pub. Date: Sep. 8, 2000

(30) Foreign Application Priority Data

Mar. 1, 1999 (AU) .............................. PP 8939

(51) Int. Cl.$^7$ .............................. A61K 39/02

(52) U.S. Cl. .............................. 424/190.1; 424/184.1; 424/185.1; 424/234.1; 530/300; 530/324; 514/2; 514/12

(58) Field of Search .............................. 530/300, 324; 514/2, 12; 424/184.1, 185.1, 190.1, 234.1

(56) References Cited

FOREIGN PATENT DOCUMENTS

| WO | 97/36923 | 10/1997 |
| WO | 98/49192 | 11/1998 |

OTHER PUBLICATIONS

Ogawa et al, "Immunobiological Activities of Synthetic . . . ," Biochemical and Biophysical Research Communications, vol. 180, No. 3 (1991).

*Primary Examiner*—L. F. Smith
*Assistant Examiner*—Robert A. Zeman
(74) *Attorney, Agent, or Firm*—Nixon & Vanderhye

(57) ABSTRACT

This invention relates to a peptide selected from the group: FLLDADHNTFGSVIPATGPLFTGTASS LYSANFESLIPANADPVVTTQNIIVTG LYSANFEYLIPANADPVVTTQNIIVTG TNPEPASGKMWIAGDGGNQP RYDDFTFEAGKKYTFTMRRAGMGDGTD DDYVFEAGKKYHFLLLMKKMGSGDGTE TNPEPASGKMWIAGDGGNQPARYDDFTFEAGKKYTFTMRRAGMGDGTD NTFGSVIPATGPL PASGKMWIAGDG EAGKKYTFTMRRA EAGKKYHFLMKKM. It also relates to compositions and use of these peptides for treating and testing *Porphyromonas gingialis*.

6 Claims, 7 Drawing Sheets

SYNTHETIC PEPTIDES CONTAINING PROTECTIVE EPITOPES FOR THE TREATMENT AND PREVENTION OF PERIODONTITIS ASSOCIATED WITH *PORPHYROMONAS GINGIVALIS*

REFERENCE TO RELATED APPLICATIONS

This application is a 371 of PCT/AU00/00142 filed Mar. 1, 2000.

FIELD OF THE INVENTION

This invention relates to an oral composition and an immunogenic composition for the suppression of the pathogenic effects of the intra-oral bacterium *Porphyromonas gingivalis* associated with periodontal disease. It also relates to diagnostic tests for the presence of *Porphyromonas gingivalis* in subgingival plaque samples and specific antibodies against *P. gingivalis* antigens in sera. The compositions comprise synthetic peptide constructs corresponding to protective epitopes of the PrtR-PrtK proteinase-adhesin complex of *Porphyromonas gingivalis*. The synthetic peptide constructs are useful as immunogens in vaccine formulations for active immunization and can be used to generate protein-specific and peptide-specific antisera useful for passive immunization and as reagents for diagnostic assays.

BACKGROUND OF THE INVENTION

Periodontal diseases are bacterial-associated inflammatory diseases of the supporting tissues of the teeth and range from the relatively mild form of gingivitis, the non-specific, reversible inflammation of gingival tissue to the more aggressive forms of periodontitis which are characterised by the destruction of the tooth's supporting structures. Periodontitis is associated with a subgingival infection of a consortium of specific Gram-negative bacteria that leads to the destruction of the periodontium and is a major public health problem. One bacterium that has attracted considerable interest is *Porphyromonas gingivalis* as the recovery of this microorganism from adult periodontitis lesions can be up to 50% of the subgingival anaerobically cultivable flora, whereas *P. gingivalis* is rarely recovered, and then in low numbers, from healthy sites. A proportional increase in the level of *P. gingivalis* in subgingival plaque has been associated with an increased severity of periodontitis and eradication of the microorganism from the cultivable subgingival microbial population is accompanied by resolution of the disease. The progression of periodontitis lesions has been demonstrated in monkey, rats and mice with the subgingival implantation of *P. gingivalis*. These findings in both animals and humans suggest a major role for *P. gingivalis* in the development of adult periodontitis.

*P. gingivalis* is a black-pigmented, anaerobic, proteolytic Gram-negative rod that obtains energy from the metabolism of specific amino acids. The microorganism has an absolute growth requirement for iron, preferentially in the form of heme or its Fe(III) oxidation product hemin and when grown under conditions of excess hemin is highly virulent in experimental animals. A number of virulence factors have been implicated in the pathogenicity of *P. gingivalis* including the capsule, adhesins, cytotoxins and extracellular hydrolytic enzymes. In order to develop an efficacious and safe vaccine to prevent *P. gingivalis* colonisation it is necessary to identify effective antigens that are involved in virulence that have utility as immunogens to generate neutralising antibodies.

We have purified and characterised a multiprotein complex of cysteine proteinase and adhesins which is a major virulence factor for *Porphyromonas gingivalis*. This complex was biochemically characterised and disclosed in International Patent Application No. PCT/AU96/00673. The complex consists of a 160 kDa Arg-specific proteinase with C-terminal adhesin domains (designated PrtR) associated with a 163 kDa Lys-specific proteinase also with C-terminal adhesin domains (designated PrtK).

SUMMARY OF THE INVENTION

The present inventors have identified a number of peptides including epitopes on the adhesins of the PrtR-PrtK complex of cysteine proteinases and adhesins which is a major virulence factor for *P. gingivalis*. These sequences are set out in Table 1.

TABLE 1

Amino acid sequences of peptides including epitopes of the PrtR-PrtK protein complex of *P. Gingivalis*.

| Designation | PrtR-PtrK Adhesin | Amino acid sequence [single letter code] |
| --- | --- | --- |
| EP1 | PrtR27 | FLLDADHNTFGSVIPATGPLFTGTASS (SEQ ID NO:1) |
| EP2 | PrtR27 | LYSANFESLIPANADPVVTTQNITVTG (SEQ ID NO:2) |
| EP3 | PrtK39 | LYSANFEYLIPANADPVVTTQNIIVTG (SEQ ID NO:3) |
| EP4 | PrtR27 | TNPEPASGKMWIAGDGGNQP (SEQ ID NO:4) |
| EP5 | PrtR27 | RYDDFTFEAGKKYTFTMRRAGMGDGTD (SEQ ID NO:5) |
| EP6 | PrtR44 | DDYVFEAGKKYHFLMKKMGSGDGTE (SEQ ID NO:6) |
| EP7 | PrtR27 | TNPEPASGKMWIAGDGGNQPARYDDFTFEAGKKY TFTMRRAGMGDGTD (SEQ ID NO:7) |

Peptides (EP1–EP7) of Table 1 represent sequences of the adhesin domains of the PrtR and PrtK protein-adhesin complex.

Accordingly, in a first aspect the present invention consists in a composition for use in raising an immune response against *Porphyromonas gingivalis*, the composition comprising a suitable adjuvant and/or acceptable carrier or excipient and at least one peptide of not more than 50 amino acids which peptide includes at least one *P. gingivalis* epitope, or multimers of said peptide, the at least one *P. gingivalis* epitope being selected from the epitopes included within a peptide selected from the group consisting of:

EP1 FLLDADHNTFGSVIPATGPLFTGTASS (SEQ ID NO:1),
EP2 LYSANFESLIPANADPVVTTQNIIVTG (SEQ ID NO:2),
EP3 LYSANFEYLIPANADPVVTTQNIIVTG (SEQ ID NO:3),
EP4 TNPEPASGKMWIAGDGGNQP (SEQ ID NO:4),
EP5 RYDDFTFEAGKKYTFTMRRAGMGDGTD (SEQ ID NO:5),
EP6 DDYVFEAGKKYHFLMKKMGSGDGTE (SEQ ID NO:6), and
EP7 TNPEPASGKMWIAGDGGNQPARYDDFTFEAGKKYTFTMRRAGMGDGTD (SEQ ID NO:7).

Where the composition includes more than one peptide the peptides may be present in the composition as individual peptides or in multimeric forms. Where multimeric forms are used the multimer may comprise multiple copies of the same peptide, however, it is preferred that the multimer includes different peptides. Peptide multimers may be prepared as described in PCT/AU98/00076, the entire contents of which are incorporated herein by reference.

In a second aspect of the present invention consists in a peptide, the peptide having not more than 50 amino acids which peptide includes at least one P. gingivalis epitope, the P. gingivalis epitope being selected from the epitopes included in the peptides selected from the group consisting of:
EP1 FLLDADHNTFGSVIPATGPLFTGTASS (SEQ ID NO:1)
EP2 LYSANFESLIPANADPVVTTQNIIVTG (SEQ ID NO:2)
EP3 LYSANFEYLIPANADPVVTTQNIIVTG (SEQ ID NO:3)
EP4 TNPEPASGKMWIAGDGGNQP (SEQ ID NO:4)
EP5 RYDDFTFEAGKKYTFTMRRAGMGDGTD (SEQ ID NO:5)
EP6 DDYVFEAGKKYHFLMKKMGSGDGTE (SEQ ID NO:6)
EP7 TNPEPASGKMWIAGDGGNQPARYDDFTFEAGKKYTFTMRRAGMGDGTD (SEQ ID NO:7)

In preferred forms of the present invention the peptide includes at least one sequence selected from the group consisting of:
NTFGSVIPATGPL (SEQ ID NO:8)
LYSANFESLIPANADPVVTTQNIIVTG (SEQ ID NO:2)
LYSANFEYLIPANADPVVTTQNIIVTG (SEQ ID NO:3)
PASGKMWIAGDG (SEQ ID NO:9)
EAGKKYTFTMRRA (SEQ ID NO:10), and
EAGKKYHFLMKKM (SEQ ID NO:11).

In another preferred embodiment of the present invention the peptide includes at least one sequence selected from the group consisting of:
FLLDADHNTFGSVIPATGPLFTGTASS (SEQ ID NO:1)
LYSANFESLIPANADPVVTTQNIIVTG (SEQ ID NO:2)
LYSANFEYLIPANADPVVTTQNIIVTG (SEQ ID NO:3)
TNPEPASGKMWIAGDGGNQP (SEQ ID NO:4)
RYDDFTFEAGKKYTFTMRRAGMGDGTD (SEQ ID NO:5)
DDYVFEAGKKYHFLMKKMGSGDGTE (SEQ ID NO:6), and
TNPEPASGKMWIAGDGGNQPARYDDFTFEAGKKYTFTMRRAGMGDGTD (SEQ ID NO:7).

In yet another preferred embodiment of the present invention the peptide is selected from the group consisting of:
FLLDADHNTFGSVIPATGPLFTGTASS (SEQ ID NO:1)
LYSANFESLIPANADPVVTTQNIIVTG (SEQ ID NO:2)
LYSANFEYLIPANADPVVTTQNIIVTG (SEQ ID NO:3)
TNPEPASGKMWIAGDGGNQP (SEQ ID NO:4)
RYDDFTFEAGKKYTFTMRRAGMGDGTD (SEQ ID NO:5)
DDYVFEAGKKYHFLMKKMGSGDGTE (SEQ ID NO:6), and
TNPEPASGKMWIAGDGGNQPARYDDFTFEAGKKYTFTMRRAGMGDGTD (SEQ ID NO:7).

As will be readily apparent to persons skilled in this area these peptides may be used as antigens in diagnostic tests or as immunogens in formulations.

In a third aspect the present invention consists in an antibody preparation comprising antibodies specifically directed against the composition of the first aspect of the invention or the peptides of the second aspect of the invention. The antibodies may be either polyclonal or monoclonal antibodies.

As will be readily apparent to persons skilled in this area these antibodies may be used in diagnostic tests or in pharmaceutical formulations.

In a fourth aspect the present invention consists in a method of reducing the prospect of P. gingivalis infection in an individual and/or severity of disease, the method comprising administering to the individual an amount of the composition of the first aspect effective to induce an immune response in the individual directed against P. Gingivalis.

In a fifth aspect the present invention consists in a method of reducing the prospect of P. gingivalis infection in an individual and/or severity of disease, the method comprising administering to the individual an effective amount of an antibody of the third aspect.

Peptides can be synthesized using one of the several methods of peptide synthesis known in the art including standard solid phase peptide synthesis using t-butyloxycarbonyl amino acids (Mitchell et al., 1978, J. Org. Chem. 43:2845–2852) using 9-fluorenylmethyloxycarbonyl (Fmoc) amino acids on a polyamide support (Druland et al., 1986, J. Chem. Soc. Perkin Trans. 1 125–137) by pepscan synthesis (Geysen et al., 1987, J. Immunol Methods 03:259; 1984, Proc. Natl. Acad. Sci. USA, 81:3998) or by standard liquid phase synthesis.

A variety of methods for the synthesis of multivalent/multipeptide high molecular weight peptide molecules can be used to synthesize the peptide antigens. This will be achieved using known in the art and novel ligation strategies.

Peptides from Table 1 can be synthesized in such a way as to contain two ligands, which can be the same or different, which may or may not be the complementary ligand. These bi-modal peptides can incorporate any ligand thus linkages such as thioether, thioester, hydrazone, oxime, thiazolidine can be utilised for the synthesis of multipeptide constructs Shao and Tam., 1995, J. Am. Chem. Soc. 117, 3893–3899, Rose, et al 1996, Bioconjugate Chem. 7(5):552–556, Rose, K., 1994, J. Am. Chem. Soc. 116:30–33, Canne., et al 1995, J. Am. Chem. Soc. 117:2998–3007, Lu., et al, 1991. Mol. Immunol 28(6):623–630, Liu and Tam., 1994, Proc. Natl. Acad. Sci. 91:6584–6588. A novel ligating strategy is to use the known reaction between thioanisole and acryloyl peptides (O'Brien-Simpson et al., 1997, J. Am. Chem. Soc. 119 (6) which results in the para substitution of thioanisole by the double bond in acidic conditions. By synthesising and mixing acryloyl-peptides and phenylthio acetyl peptides and exposing them to acidic conditions ligation can proceed by Friedal-Craft alkylation. Ligation can be accomplished between peptides and on to an oligolysine support derivatised with one of the ligands. Conditions for ligation can consist of: Friedal-Craft reaction conditions which are known in the art and known peptide cleavage conditions.

The introduction of ligand groups to form bi-modal peptides can be achieved by coupling a ligand on to free amino groups, which is known in the art, at the N- or C-terminus of a peptide or within the peptide sequence. This can be achieved by coupling eg. Fmoc(Fmoc) 2.3 diamino propionic acid or Fmoc Lys (Fmoc)-OH or orthogonally protected lysine residues such as Fmoc Lys (Mtt)-OH using standard peptide coupling protocols on to the N-terminus or introduced at the C-terminus or within the peptide sequence. After deprotection, ligand groups can be coupled on to the amino groups and by selective deprotection of eg. Fmoc Lys (Mtt) different ligands can be coupled on to a single peptide. At any point in the synthesis spacer moieties can be introduced between the peptide and the ligands and/or between the ligands, which may be used to reduce steric hindrance in the ligation reaction. FIG. 1 shows the synthesis protocol.

Peptide ligation can be achieved in solution or on the solid phase. The incorporation of different ligands and selective protection of one ligand can allow the synthesis of multivalent, multipeptide constructs, where by, peptides are ligated sequentially. This strategy has the advantage that the orientation and order of peptides ligated is known and can be controlled. Protecting groups for ligands can be for example Fmoc, allyloxycarbonyl (Aloc) or nitrocinnamyloxycarbonyl (Noc) which are stable to standard cleavage conditions but are easily removed under basic conditions or catalytic allyl transfer. FIG. 2 shows the ligation scheme for the synthesis of multivalent peptide constructs using bi-modal peptides. The protocol can be adapted for a variety of ligation chemistries by simply altering the ligands which are coupled to the peptide to form the bi-modal peptide.

The step wise addition of each peptide can be achieved on the solid phase. This can be achieved by synthesising a peptide on to the solid support via a base labile handle eg. 4-hydroxymethyl benzoic acid. This can allow full side chain deprotection of the peptide with the peptide remaining attached to the solid support. This would allow ligation to still be carried out in aqueous solvents similar to those used for solution phase ligation except that separation of the ligand product from unreacted bi-modal peptide can be achieved by simply washing the solid support. The reaction can be monitored by ninhydrin or trinitrobenzene sulphonic acid tests, where by, lysine residues within the bi-modal peptide would need to be protected eg. with (4,4-dimethyl-2,6-dioxocyclohex-1-ylidene)ethyl (Dde) which is stable to acid cleavage but can be removed with hydrazine. FIG. 3 shows the ligation strategy for the solid phase.

Bi-modal peptides can be synthesized so that ligands are at the N- and C-terminus. This would allow the preparation of cyclic peptides and the formation of di-peptide constructs where by peptides can run parallel or anti parallel to each other by either coupling N- to N- and C- to C-termini or N- to C-termini together respectively (FIG. 4).

Another technique for the synthesis of multivalent peptide constructs is to ligate peptides on to an oligolysine support (Rose, et al 1996, Bioconjugate Chem. 7(5):552–556, Canne., et al 1995, J. Am. Chem. Soc. 117:2998–3007 and Lu., et al, 1991, Mol. Immunol 28(6):623–630). By incorporating a number of different ligands and or protected ligands on to the lysine support, peptides can be ligated to a particular position on the support. Ligation chemistries such as oxime or hydrazone with haloacylation and Friedal-Craft alkylation can be used sequentially without the need for ligand protection. Ligand protection can be used to increase the number of different peptides incorporated on to the lysine support. FIG. 5 demonstrates the synthesis protocol.

Another method known in the art is the synthesis of acryloyl peptides and their polymerisation with acrylamide (O'Brien-Simpson et al., 1997, J. Am. Chem. Soc. 119 (6)) or acryloyl amino acids. Peptides from the PrtR-PrtK protein complex listed in Table 1 can be acryloylated and polymerised either singularly or in combination. Although this method allows the polymerisation of a number of peptides together the order in which peptides are incorporated can not be controlled.

The final peptide construct may or may not contain all, sum or part of the peptides listed in Table 1. Also the construct may or may not contain promiscuous T-cell epitopes known in the art (Kaumaya et al 1994, in Solid Phase Synthesis, Ed Epton, R) or a derived sequence from structural/binding motifs of MHC class II binding peptides (O'Sullivan et al., 1991, J. Immunol, 147:2663–2669, Hammer et al., 1993, Cell, 74:197–203 and Alexander et al., 1994, Immunity, 1:751–761). Furthermore, lipid moieties such as palmitic acid or cholesterol can be included to enhance the immunogenic properties of the peptide construct. Enzymatic cleavable sequences known in the art (Duncan et al., ref) or derived sequences from cleavage motifs (Van Noort and van der Drift., ref) can also be incorporated with the peptide construct.

The synthetic peptide antigens identified in Table 1 are of particular interest for diagnostic and neutralisation by passive immunity through oral compositions containing neutralising antibodies and by vaccine development. The superiority of these synthetic peptide antigens to prior disclosed *P. gingivalis* antigens, is that these peptides have been demonstrated to react with protective sera from animals and humans. The peptides represent sequences in the adhesin domains of the PrtR and PrtK which make them ideal for the development of diagnostic and immunoprophylactic products.

Antibodies against the antigens can be used in oral compositions such as toothpaste and mouthwash to neutralise the antigens and thus prevent disease. Antigen-specific antibodies can also be used for the early detection of *P. gingivalis* in subgingival plaque samples by a diagnostic assay. A vaccine based on these antigens and suitable adjuvant delivered by nasal spray, orally or by injection to produce a specific immune response against these antigens thereby reducing colonisation and virulence of *P. gingivalis* and thereby preventing disease. The peptide antigens of the present invention may be used as immunogens in prophylactic and/or therapeutic vaccine formulations; or as an antigen in diagnostic immunoassays directed to detection of *P. gingivalis* infection by measuring an increase in serum titer of *P. gingivalis*-specific antibody. Also the synthetic peptides of the present invention may be used to generate antigen-specific antibody which may be useful for passive immunization and as reagents for diagnostic assays directed to detecting the presence of *P. gingivalis* in clinical specimens such as subgingival plaque samples.

As mentioned it is preferred that the composition includes an adjuvant. As will be understood an "adjuvant" means a composition comprised of one or more substances that enhances the immunogenicity and efficacy of a vaccine composition. Non-limiting examples of suitable adjuvants include squalane and squalene (or other oils of animal origin); block copolymers; detergents such as Tween®-80; Quil® A, mineral oils such as Drakeol or Marcol. vegetable oils such as peanut oil; *Corynebacterium*-derived adjuvants such as *Corynebacterium parvum; Propionibacterium*-derived adjuvants such as *Propionibacterium acne; Mycobacterium bovis* (Bacille Calmette and Guerin or BCG); interluekins such as interluekin 2 and interleukin 12; monokines such as interleukin 1; tumour necrosis factor; interferons such as gamma interferon; combinations such as saponin-aluminium hydroxide or Quil-A aluminium hydroxide; liposomes; ISCOM adjuvant; mycobacterial cell wall extract; synthetic glycopeptides such as murarmyl dipeptides or other derivatives; Avridine; Lipid A derivatives; dextran sulfate; DEAE-Dextran or with aluminium phosphate; carboxypolymethylene such as Carbopol' EMA; acrylic copolymer emulsions such as Neocryl A640 (e.g. U.S. Pat. No. 5,047,238); vaccinia or animal poxvirus proteins; sub-viral particle adjuvants such as cholera toxin, or mixtures thereof.

DETAILED DESCRIPTION OF THE INVENTION

Figure 1:
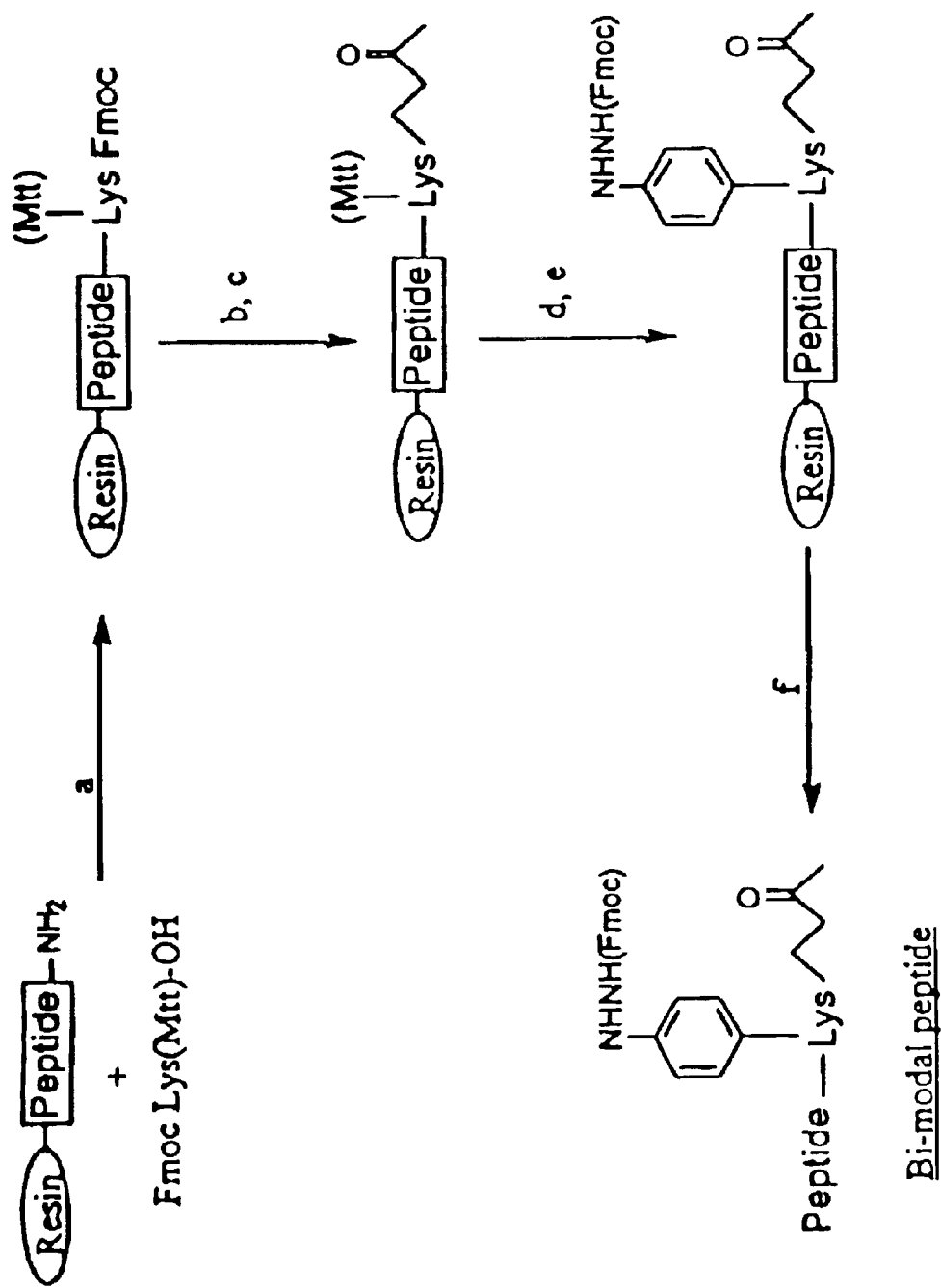
FIG. 1: Synthesis of Bi-modal Peptides Although a specific example is shown here any ligand can be introduced at the a or e amino groups of lysine. (a) acylation e.g. amino acid:HOBt:HBTU:DIPEA 1:1:1:1.5 in dimethyl formamide (DMF). (b) Fmoc deprotection e.g. 20% piperidine in DMF. (c) Levulinic acid:diisopropyl carbodiimide (DIC) 2:1 in dichloromethane (DCM), 1 h. (d) Mtt removal, 3×1% TFA in DCM, 3 mins. (e) Fmoc-Hydrazino benzoic acid:DIC 2:1, in DCM, 1 h. (f) Acid cleavage e.g. TFA:water 95:5.
Figure 2:
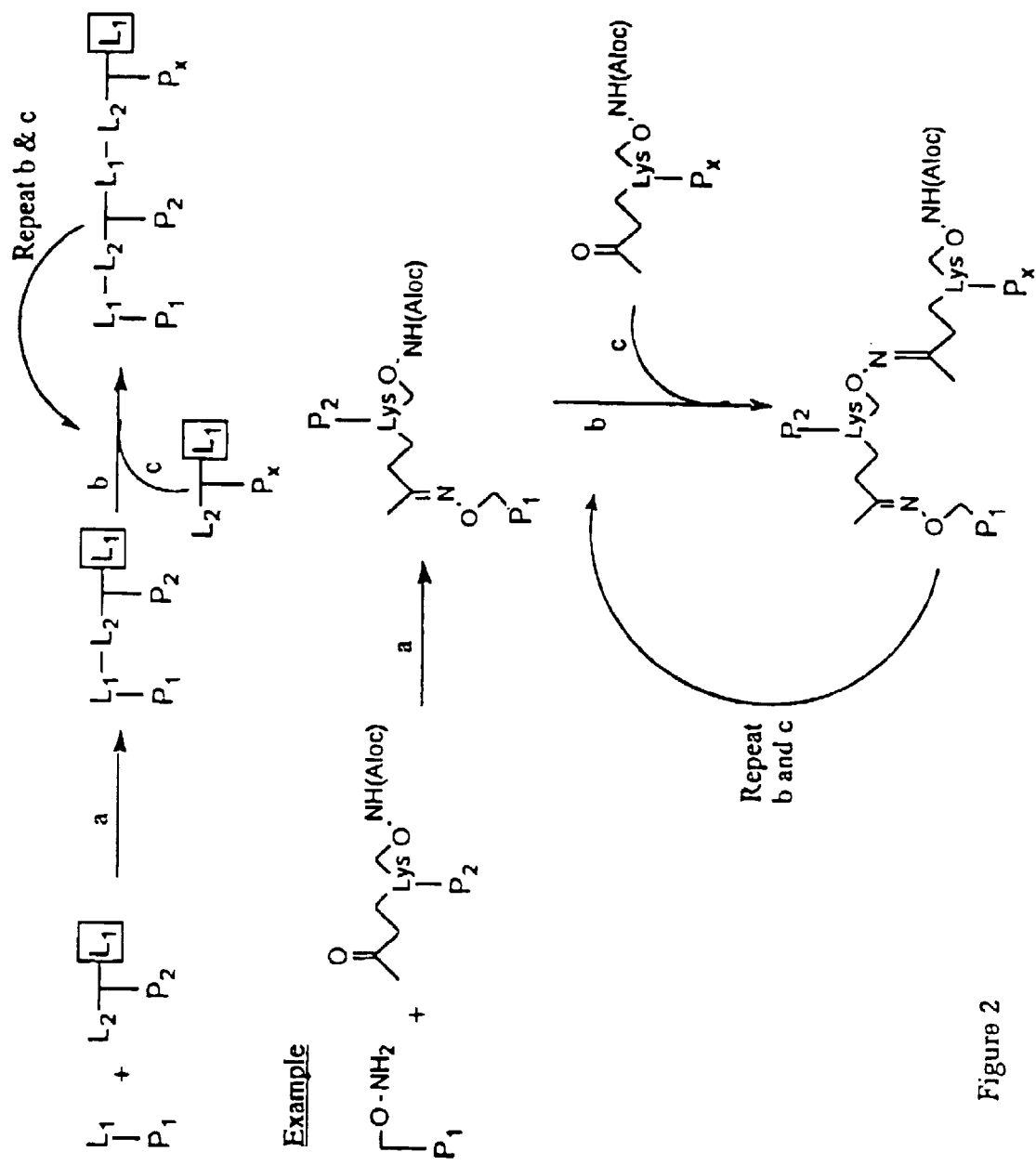
FIG. 2: Synthesis of multivalent peptide constructs using bi-modal peptides. (a) Ligation. 8 M urea and 0.1 M $NaH_2PO_4$ (pH range 3–4.7). Ligation can be monitored by reverse phase analytical HPLC and mass spectrometry. (b) Deprotection, e.g. Aloc is removed by palladium(0)-catalyzed allyl group transfer to a basic receptor. The ligation product can be purified by preparative HPLC and lyophilised. (c) Ligation. Similar conditions as described in (a). Different ligation chemistries can be used by synthesising peptides with different ligands and synthesising non-complementary ligands on to the same peptide, thereby avoiding proected ligands. The square symbol indicates protection, (L) ligand, (P) peptide.
Figure 3:
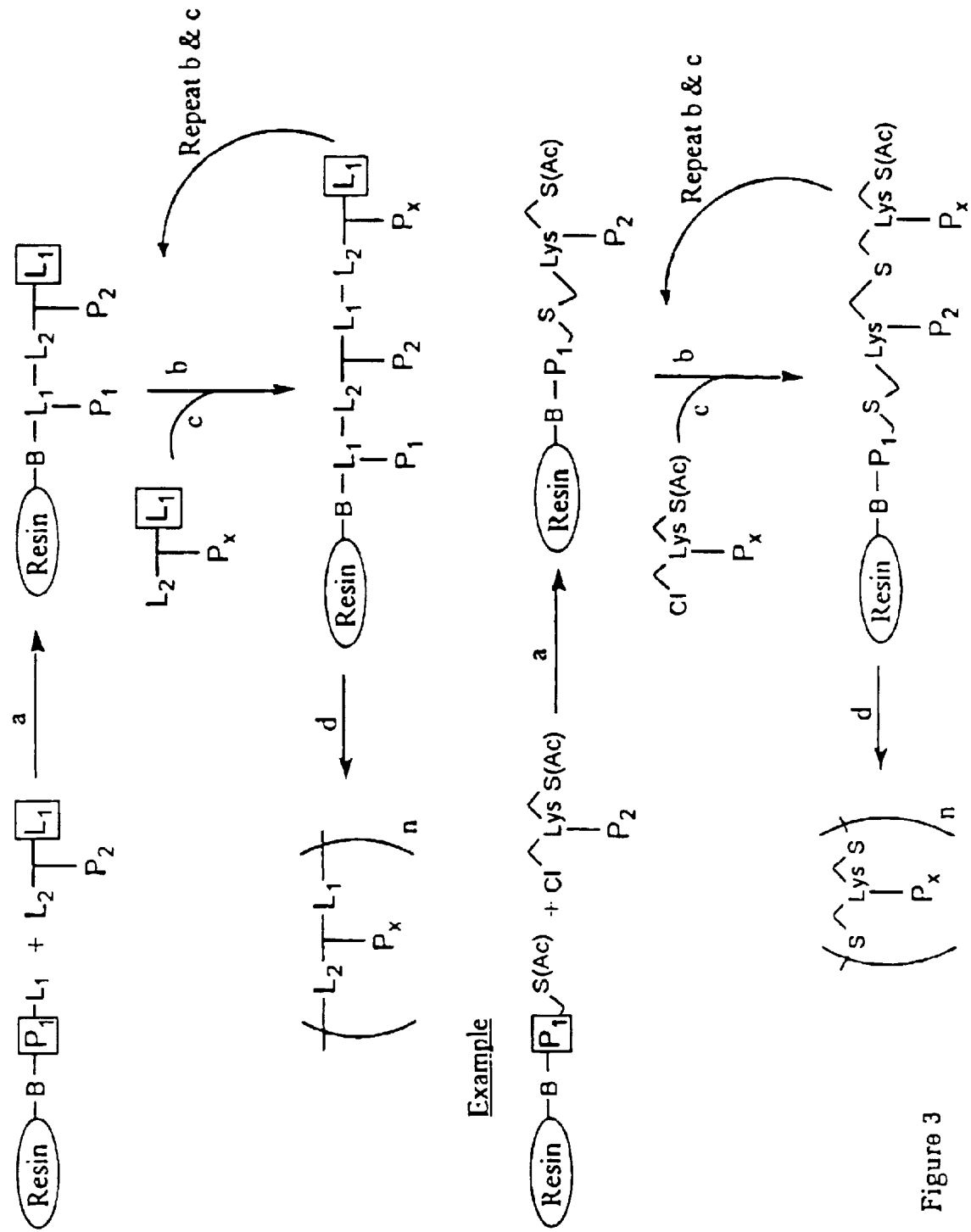
FIG. 3: Synthesis of multivalent peptide constructs using bi-modal peptides by solid phase. (a) Deprotection and ligation. The S-acetyl protecting group is removed by aqueous hydroxyamine 0.05 M, pH 7.3. After washing the first peptide can be ligated on to the SH group, 6 M aqueous guanidine hydrochloride and 0.05 M EDTA pH 6.4–6.5 adjusted by 1 M Tris.HCl under nitrogen. Ligation buffer can contain organic solvents such as acetonitrile. (b) Deprotection, the S-acetyl protecting group can be removed by aqueous hydroxyamine 0.05 M, pH 7.3. (c) Ligation, as described in (a) although different ligation chemistries can be used by synthesising peptides with different ligands and synthesising non-complementary ligands on to the same peptide, thereby avoiding proected ligands. The square symbol indicates protection, (L) ligand, (P) peptide, (B) base labile handle, 4-hydroxymethyl benzoic acid.
Figure 4:
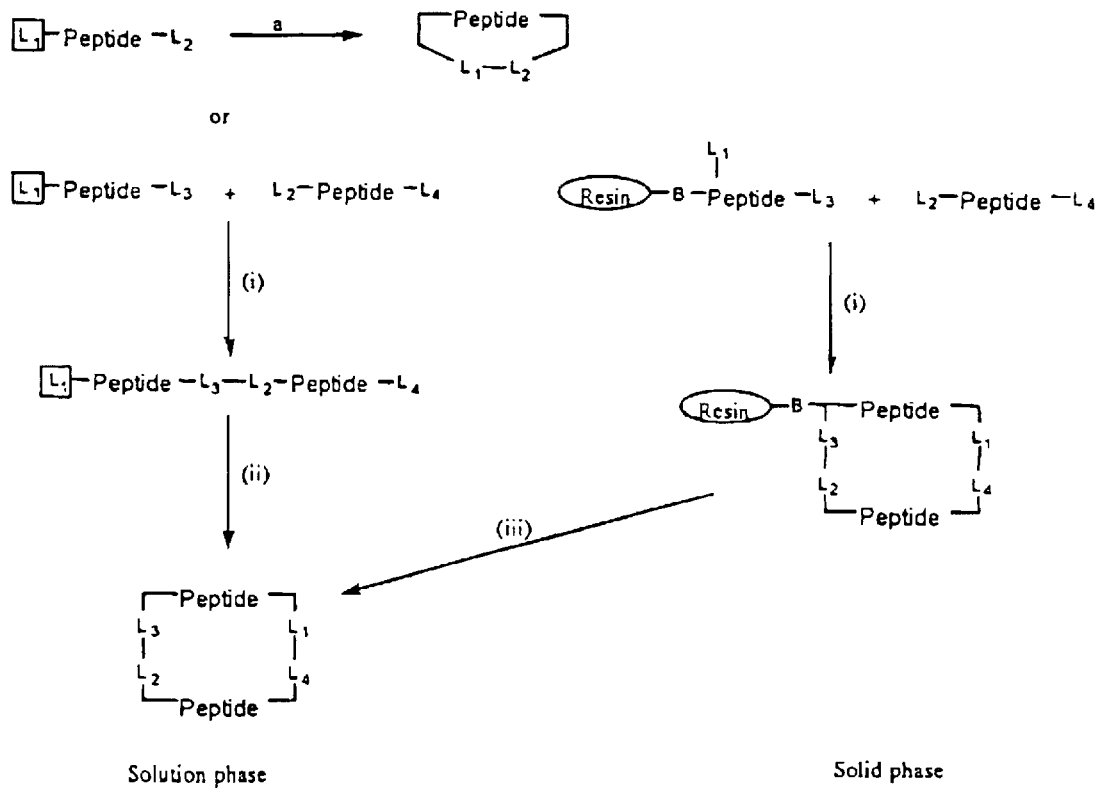
FIG. 4: Cyclization using bi-modal peptides. (a) Deprotection and cyclisation. Synthesis of bi-modal peptides which have complimentary ligands at their N- and C-termini allows the cyclisation of these peptides in aqueous buffers (i) Ligation. (ii) Deprotection and ligaction. (iii) Cleavage of the cyclic peptide from the base labile handle. Example; The peptides shown are from Table 1 and represent major protective epitopes on PrtR 27 or PrtK39 (SEQ ID NO:4 and SEQ ID NO:5). (a) Ligation, 95% aqueous TFA. Ligation can be monitored by reverse phase analytical HPLC and mass spectrometry. Ligation conditions can be varied to include scavengers commonly used in peptide synthesis and different acidic conditions to enhance the Friedal-Craft alkylation. (b) Deprotection and ligation. The S-acetyl protecting group can removed by aqueous hydroxyamine 0.05 M, pH 7.3. Ligation, 6 M aqueous guanidine hydrochloride and 0.05 M EDTA pH 6.4–6.5 adjusted by 1 M Tris.HCl under nitrogen. The ligation straegy can also be accomplished on the solid phase. By selecting which ligand to introduce at the N- and C- terminal parallel and anti-parallel cyclic peptides can be synthesised.
Figure 4:
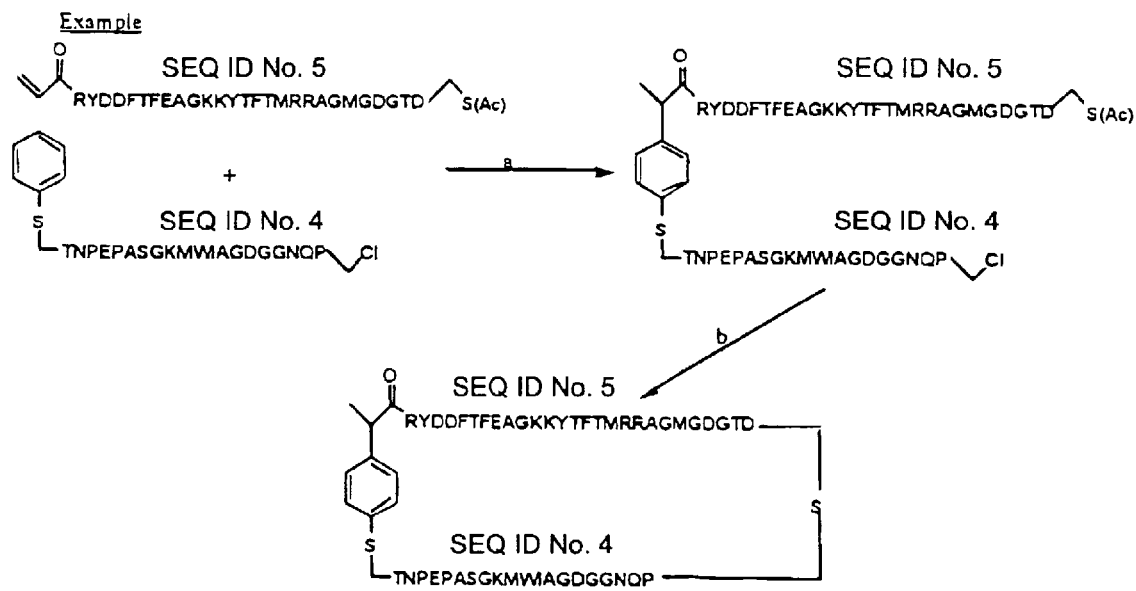
Figure 5:
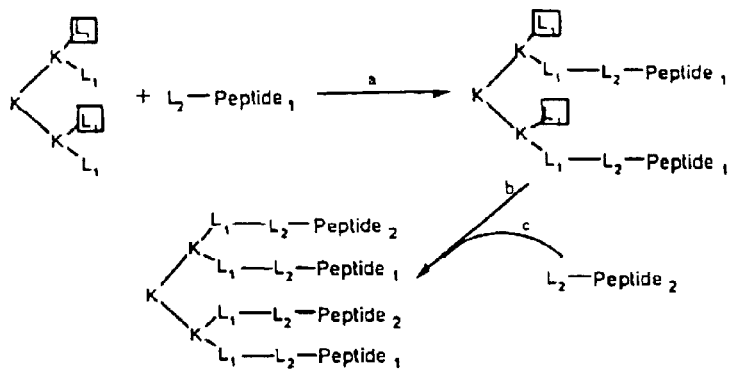
FIG. 5: Synthesis of multivalent multiple antigenic peptides (MAPs) using alternate ligation chemistries (SEQ ID NO:4 and SEQ ID NO:5). By using different ligation strategies a vareity of peptides can be ligated onto a single multiple antigenic peptide. The example shown is of peptides listed in Table 1. (a) Ligation, 95% aqueous TFA. Ligation can be monitored by reverse phase analytical HPLC and mass spectrometry. Deprotection, Aloc can removed by palladium(0)-catalyzed allyl group transfer to a basic receptor, after purifiction the second peptide can be ligated on to the MAP, (c) 8 M urea and 0.1 M $NaH_2PO_4$ (pH range 3–4.7).
Figure 5:
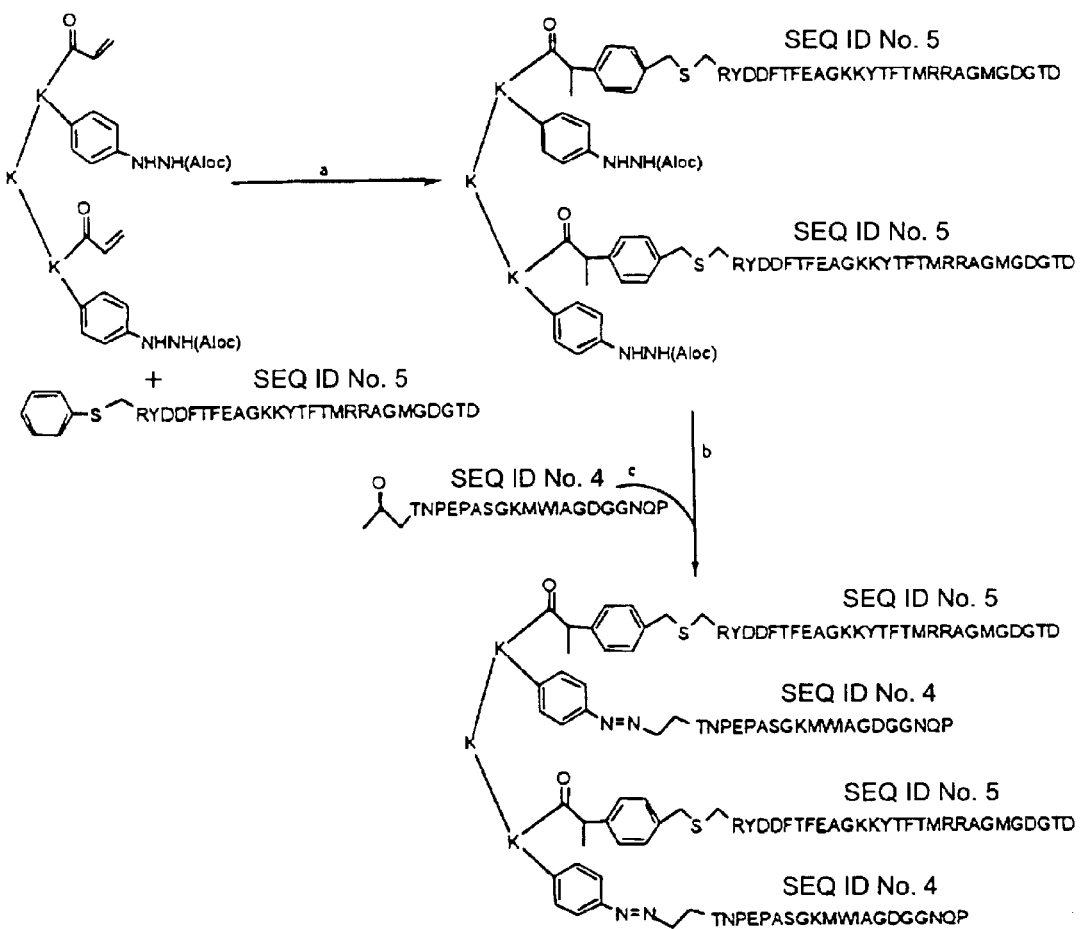

This invention relates to an oral composition and a vaccine for the suppression of the pathogenic effects of the intra-oral bacterium Porphyromonas gingivalis associated with periodontal disease. It also relates to diagnostic tests for the presence of Porphyromonas gingivalis in subgingival plaque samples and specific anti-P. gingivalis antibodies in sera. The peptide antigens of Table 1 can be synthesized individually or as multimetric or multipeptide constructs.

The synthetic peptide antigens are used to generate polyclonal or monoclonal antibodies using standard techniques. The animals used for antibody generation can be mice, rabbits, goats, chickens, sheep, horses, cows etc. When a high antibody titre against the antigens is detected by immunoassay the animals are bled or eggs or milk are collected and the serum prepared and/or antibody purified using standard techniques or monoclonal antibodies produced by fusing spleen cells with myeloma cells using standard techniques. The antibody (immunoglobulin fraction) may be separated from the culture or ascites fluid, serum, milk or egg by salting out, gel filtration, ion exchange and/or affinity chromatography, and the like, with salting out being preferred. In the salting out method the antiserum or the milk is saturated with ammonium sulphate to produce a precipitate, followed by dialyzing the precipitate against physiological saline to obtain the purified immunoglobulin fraction with the specific antibody. The preferred antibody is obtained from the equine antiserum and the bovine antiserum and milk. In this invention the antibody contained in the antiserum and milk obtained by immunising the animal with the antigens is blended into the oral composition. In this case the antiserum and milk as well as the antibody separated and purified from the antiserum and milk may be used. Each of these materials may be used alone or in combination of two or more. Antibodies can be used in oral compositions such as toothpaste and mouthwash to neutralise P. gingivalis and thus prevent disease. The antibodies can also be used for the early detection of P. gingivalis in subgingival plaque samples by a chairside Enzyme Linked Immunosorbent Assay (ELISA).

For oral compositions it is preferred that the amount of the above antibodies administered is 0.0001–50 g/kg/day and that the content of the above antibodies is 0.0002–10% by weight preferably 0.002–5% by weight of the composition. The oral composition of this invention which contains the above-mentioned serum or milk antibody may be prepared and used in various forms applicable to the mouth such as dentifrice including toothpastes, toothpowders and liquid dentifrices, mouthwashes, troches, chewing gums, dental pastes, gingival message creams, gargle tablets, dairy products and other foodstuffs. The oral composition according to this invention may further include additional well known ingredients depending on the type and form of a particular oral composition.

In certain highly preferred forms of the invention the oral composition may be substantially liquid in character, such as a mouthwash or rinse. In such a preparation the vehicle is typically a water-alcohol mixture desirably including a humectant as described below. Generally, the weight ratio of water to alcohol is in the range of from 1:1 to about 20:1. The total amount of water-alcohol mixture in this type of preparation is typically in the range of from about 70 to about 99.9% by weight of the preparation. The alcohol is typically ethanol or isopropanol. Ethanol is preferred.

The pH of such liquid and other preparations of the invention is generally in the range of from about 4.5 to about 9 and typically from about 5.5 to 8. The pH is preferably in the range of from about 6 to about 8.0, preferably 7.4. The pH can be controlled with acid (e.g. citric acid or benzoic acid) or base (e.g. sodium hydroxide) or buffered (as with sodium citrate, benzoate, carbonate, or bicarbonate, disodium hydrogen phosphate, sodium dihydrogen phosphate, etc).

Other desirable forms of this invention, the oral composition may be substantially solid or pasty in character, such as toothpowder, a dental tablet or a dentifrice, that is a toothpaste (dental cream) or gel dentifrice. The vehicle of such solid or pasty oral preparations generally contains dentally acceptable polishing material. Examples of polishing materials are water-insoluable sodium metaphosphate, potassium metaphosphate, tricalcium phosphate, dihydrated calcium phosphate, anhydrous dicalcium phosphate, calcium pyrophosphate, magnesium orthophosphate, trimagnesium phosphate, calcium carbonate, hydrated alumina, calcined alumina, aluminum silicate, zirconium silicate, silica, bentonite, and mixtures thereof. Other suitable polishing material include the particulate thermosetting resins such as melamine-, phenolic, and urea-formaldehydes, and cross-linked polyepoxides and polyesters. Preferred polishing materials include crystalline silica having particle sized of up to about 5 microns, a mean particle size of up to about 1.1 microns, and a surface area of up to about 50,000 cm$^2$/gm., silica gel or colloidal silica, and complex amorphous alkali metal aluminosilicate.

When visually clear gels are employed, a polishing agent of colloidal silica, such as those sold under the trademark SYLOID as Syloid 72 and Syloid 74 or under the trademark SANTOCEL as Santocel 100, alkali metal alumino-silicate complexes are particularly useful since they have refractive indices close to the refractive indices of gelling agent-liquid (including water and/or humectant) systems commonly used in dentifrices.

Many of the so-called "water insoluble" polishing materials are anionic in character and also include small amounts of soluble material. Thus, insoluble sodium metaphosphate may be formed in any suitable manner as illustrated by Thorpe's Dictionary of Applied Chemistry, Volume 9, 4th Edition, pp. 510–511. The forms of insoluble sodium metaphosphate known as Madrell's salt and Kurrol's salt are further examples of suitable materials. These metaphosphate salts exhibit only a minute solubility in water, and therefore are commonly referred to as insoluble metaphosphates (IMP). There is present therein a minor amount of soluble phosphate material as impurities, usually a few percent such as up to 4% by weight. The amount of soluble phosphate material, which is believed to include a soluble sodium trimetaphosphate in the case of insoluble metaphosphate, may be reduced or eliminated by washing with water if desired. The insoluble alkali metal metaphosphate is typically employed in powder form of a particle size such that no more than 1% of the material is larger than 37 microns.

The polishing material is generally present in the solid or pasty compositions in weight concentrations of about 10% to about 99%. Preferably, it is present in amounts from about 10% to about 75% in toothpaste, and from about 70% to about 99% in toothpowder. In toothpastes, when the polishing material is silicious in nature, it is generally present in amount of about 10–30% by weight. Other polishing materials are typically present in amount of about 30–75% by weight.

In a toothpaste, the liquid vehicle may comprise water and humectant typically in an amount ranging from about 10% to about 80% by weight of the preparation. Glycerine, propylene glycol, sorbitol and polypropylene glycol exemplify suitable humectants/carriers. Also advantageous are liquid mixtures of water, glycerine and sorbitol. In clear gels where the refractive index is an important consideration, about 2.5–30% w/w of water, 0 to about 70% w/w of glycerine and about 20–80% w/w of sorbitol are preferably employed.

Toothpaste, creams and gels typically contain a natural or synthetic thickener or gelling agent in proportions of about 0.1 to about 10, preferably about 0.5 to about 5% w/w. A suitable thickener is synthetic hectorite, a synthetic colloidal magnesium alkali metal silicate complex clay available for example as Laponite (e.g. CP, SP 2002, D) marketed by Laporte Industries Limited. Laponite D is, approximately by weight 58.00% SiO$_2$, 25.40% MgO, 3.05% Na$_2$O, 0.98% Li$_2$O, and some water and trace metals. Its true specific gravity is 2.53 and it has an apparent bulk density of 1.0 g/ml at 8% moisture.

Other suitable thickeners include Irish moss, iota carrageenan, gum tragacanth, starch, polyvinylpyrrolidone, hydroxyethylpropylcelllose, hydroxybutyl methyl cellulose, hydroxypropyl methyl cellulose, hydroxyethyl cellulose (e.g. available as Natrosol), sodium carboxymethyl cellulose, and colloidal silica such as finely ground Syloid (e.g. 244). Solubilizing agents may also be included such as humectant polyols such propylene glycol, dipropylene glycol and hexylene glycol, cellosolves such as methyl cellosolve and ethyl cellosolve, vegetable oils and waxes containing at least about 12 carbons in a straight chain such as olive oil, castor oil and petrolatum and esters such as amyl acetate, ethyl acetate and benzyl benzoate.

It will be understood that, as is conventional, the oral preparations are to be sold or otherwise distributed in suitable labelled packages. Thus, a jar of mouthrinse will have a label describing it, in substance, as a mouthrinse or mouthwash and having directions for its use; and a toothpaste, cream or gel will usually be in a collapsible tube, typically aluminium, lined lead or plastic, or other squeeze, pump or pressurized dispenser for metering out the contents, having a label describing it, in substance, as a toothpaste, gel or dental cream.

Organic surface-active agents are used in the compositions of the present invention to achieve increased prophylactic action, assist in achieving thorough and complete dispersion of the active agent throughout the oral cavity, and render the instant compositions more cosmetically acceptable. The organic surface-active material is preferably anionic, nonionic or ampholytic in nature which does not denature the antibody of the invention, and it is preferred to employ as the surface-active agent a detersive material which imparts to the composition detersive and foaming properties while not denaturing the antibody. Suitable examples of anionic surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkylsulfo-acetates, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine which should be substantially free from soap or similar higher fatty acid material. The use of these sarconite compounds in the oral compositions of the present invention is particularly advantageous since these materials exhibit a prolonged marked effect in the inhibition of acid formation in the oral cavity due to carbohydrates breakdown in addition to exerting some reduction in the solubility of tooth enamel in acid solutions. Examples of water-soluble nonionic surfactants suitable for use with antibodies are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides, polyhydric alcohols (e.g. sorbitan monostearate) and polypropyleneoxide (e.g. Pluronic materials).

Surface active agent is typically present in amount of about 0.1–5% by weight. It is noteworthy, that the surface active agent may assist in the dissolving of the antibody of the invention and thereby diminish the amount of solubilizing humectant needed.

Various other materials may be incorporated in the oral preparations of this invention such as whitening agents, preservatives, silicones, chlorophyll compounds and/or ammoniated material such as urea, diammonium phosphate, and mixtures thereof. These adjuvants, where present, are incorporated in the preparations in amounts which do not substantially adversely affect the properties and characteristics desired.

Any suitable flavoring or sweetening material may also be employed. Examples of suitable flavoring constituents are flavoring oils, e.g. oil of spearmint, peppermint, wintergreen, sassafras, clove, sage, eucalyptus, marjoram, cinnamon, lemon, and orange, and methyl salicylate. Suitable sweetening agents include sucrose, lactose, maltose, sorbitol, xylitol, sodium cyclamate, perillartine, AMP (aspartyl phenyl alanine, methyl ester), saccharine, and the like. Suitably, flavor and sweetening agents may each or together comprise from about 0.1% to 5% more of the preparation.

In the preferred practice of this invention an oral composition according to this invention such as mouthwash or dentifrice containing the composition of the present invention is preferably applied regularly to the gums and teeth, such as every day or every second or third day or preferably from 1 to 3 times daily, at a pH of about 4.5 to about 9, generally about 5.5 to about 8, preferably about 6 to 8, for at least 2 weeks up to 8 weeks or more up to a lifetime.

The compositions of this invention can be incorporated in lozenges, or in chewing gum or other products, e.g. by stirring into a warm gum base or coating the outer surface of a gum base, illustrative of which may be mentioned jelutong, rubber latex, vinylite resins, etc., desirably with conventional plasticizers or softeners, sugar or other sweeteners or such as glucose, sorbitol and the like.

Another important form of the invention is a vaccine based on the synthetic peptide antigens and suitable adjuvant delivered by nasal spray, orally or by injection to produce a specific immune response against the antigen thereby reducing colonisation of P. gingivalis and reducing virulence thereby preventing disease. Unlike whole P. gingivalis cells or other previously prepared antigens, the peptide antigens described herein are safe and effective antigens for the preparation of a vaccine for the prevention of P. gingivalis-associated periodontal disease. Additionally, according to the present invention, antigenic peptide produced may be used to generate P. gingivalis antisera useful for passive immunization against periodontal disease and infections caused by P. gingivalis.

The following examples are further illustrative of the nature of the present invention, but it is understood that the invention is not limited thereto. All amounts and proportions referred to herein and in the appended claims are by weight unless otherwise indicated.

EXAMPLE 1

(i) Identification of Protective Epitopes in the PrtR-PrtK Proteinase-Adhesin Complex The PrtR-PrtK proteinase-adhesin complex was purified as described previously in International Patent Application No. PCT/AU96/00673 and was shown to confer protection to mice against challenge with P. gingivalis when used as a vaccine. The PrtR-PrtK complex was tested in the mouse abscess model. This model is loosely based on the methods of Kesavalu et al. (1992) (Infect Immun 60: 1455–1464). A typical experiment is outlined below. Briefly BALB/c mice were obtained from ARC (Perth, Australia) and were immunised subcutaneously in the scruff of the neck with the preparations and doses according to Table 2 before challenge with live P. gingivalis strain W50, which was given at 10 weeks of age. Mice were given 2 doses of vaccine at 4 and 1 weeks before challenge. Formalin killed P. gingivalis W50 cells were prepared by incubating an aliquot of cells in 0.5% (vol/vol) of buffered formol saline overnight at 4° C. All preparations were emulsified with an equal volume of Freund's Incomplete Adjuvant (FIA, Sigma) prior to injection. Animals were bled before and 1 week after the immunisation schedule. Sera were screened by ELISA and using a P. gingivalis sonicate as the adsorbed antigen.

TABLE 2

| | | Immunization schedule | |
|---|---|---|---|
| Group | No. of Doses | Treatment | n |
| 1 | 2 | $1 \times 10^9$ Formalin killed P. gingivalis cells in FIA[1] | 11 |
| 2 | 2 | Affinity purified P. gingivalis PrtR-PrtK complex in FIA | 5 |
| 3 | 2 | Tris-cysteine buffer in FIA | 10 |
| 4 | 2 | Tris-cysteine buffer | 10 |

[1]FIA = Freund's incomplete adjuvant

For the preparation of the bacterial challenge P. gingivalis cells were grown at 37° C. on lysed horse blood agar (HBA) plates until day 3 or 4 in an anaerobic chamber (Mark 3

Anaerobic Workstation, Don Whitley Scientific Limited; with an air mixture of 8% $H_2$, 12% $CO_2$, 80% $N_2$), then passaged into 20 ml of brain heart infusion broth (BHIB: Oxoid) supplemented with 0.5 g/L cysteine and 1 mg/L haemin for 24 hours in a standard incubator at 37° C. Finally, 3 ml of this culture was added to 400 ml of BHIB-cysteine media and incubated for approximately 15 hours in a standard incubator at 37° C., until the optical density at 650 nm reached 0.18. The cells were then pelleted by centrifugation at 10,000 g for 30 minutes using a JA10 rotor in a Beckman High Speed centrifuge and then resuspended to a final dilution of $3 \times 10^{30}$ cells per ml in BHIB-cysteine media according to previously established growth curves for the W50 strain used in these experiments. Mice were marked for identification, their backs and chests shaved to make measurement of lesions possible, then weighed prior to inocculation with the challenge dose at a single site in the middle of the back. A 0.1 ml dose was given representing a predicted challenge dose of $3 \times 10^9$ bacteria per mouse. The inoculum dose was confirmed by culturing various dilutions of the challenge dose on lysed HBA plates and examining the number of colonies 7 days later.

Following challenge mice were examined daily for the number and size of lesions on their body and their size estimated by measuring the approximate surface area in $mm^2$ involved. Previous experiments had shown that in unimmunized mice, lesions developed on the belly of the mice following inoculation of live bacteria into the back or side. Any distressed animals were culled. Observations were carried out over two weeks and a summary of one such experiment is summarised below in Table 3. In this experiment while a dose of $3 \times 10^9$ bacteria per mouse was the desired number of bacteria, after plating out of the inoculum it was calculated that each mouse actually received a challenge dose of $3.17 \times 10^9$ live *P. gingivalis* bacteria strain W50.

When mice were immunised significant reductions ($p < 0.005$) were seen in the size of the lesions with whole formalin killed *P. gingivalis* strain W50 cells (Group 1), and the PrtR-PrtK complex (Group 2) when compared with the lesion size of the animals receiving FIA (Group 3) (Table 3). These results clearly show that the PrtR-PrtK complex works effectively as an immunogen. The only group of animals that had a number of animals (40%) that exhibited no visible lesions at all was the PrtR-PrtK complex group (Group 2). All other groups, including formalin killed cells (Group 1), had all animals exhibiting visible lesions indicating that the PrtR-PrtK complex was a better immunogen than formalin killed cells.

TABLE 3

Immunisation with the PrtR-Prtk complex can protect mice from challenge with *P. gingivalis*

| Group | Lesion size Mean maximum lesion size $mm^2$ | P* |
|---|---|---|
| 1 | 30.2 ± 28.4† | 0.0008 |
| 2 | 30.0 ± 36.0 | 0.0028 |
| 3 | 86.8 ± 41.1 | — |
| 4 | 201.7 ± 125.8 | 0.012 |

*probability calculated by Mann Whitney rank sum test comparing Group 3 with other groups.
†mean ± SD The protective sera from Group 2 mice immunized with the PrtR-PrtK complex was collected and pooled and used in a Western Blot with the PrtR-PrtK immunogen. As well as the mice protective sera a Western blot was also carried out using sera from two patients with periodontitis (D24, D20) and a healthy patient (H10) with no signs of periodontitis but who harboured *P. gingivalis* in sub-gingival plaque. Patient D20 had severe advanced periodontitis whereas patient D24 has only low levels of disease.

Immunoblotting

Purified PrtR-PrtK complex was subjected to SDS-PAGE using 12.5% acrylamide gels (1 mm) in a mini-gel system (BioRad, Richmond, Calif.). Proteins were electrophoretically transferred onto PVDF membrane. After sectioning of the membrane the molecular weight standards were stained with 0.1% w/v CBB R250. The remaining sections were blocked for 1 hour at 20° C. with 5% w/v non-fat skim milk powder in TN buffer (50 mM Tris-HCl, pH 7.4, 100 mM NaCl). Sections were subsequently incubated with the following antisera diluted 1:25 with TN buffer; patient H10, patient D24, patient D20 or mouse protective anti PrtR-PrtK sera. After five hours at 20° C. the sections were washed (4×TN buffer containing 0.05% v/v Tween 20) and then incubated for an hour at 20° C. with the appropriate conjugate antibody; anti-human IgG horse radish peroxidase conjugate or anti-mouse IgG horse radish peroxidase conjugate. After washing (4×TN buffer containing 0.05% v/v Tween 20) bound antibody was detected with 2.8 M 4-chloro-1-napthol in TN buffer containing 16.6% v/v methanol and 0.05% v/v of a 30% $H_2O_2$ solution. Colour development was stopped by rinsing the membranes with Milli Q water.

A protein band at 44 kDa was shown to react with all of the sera tested (data not shown). The protective mouse sera and sera from patient H10 who does not have periodontitis also bound to a protein band of 27 kDa (PrtR27 adhesin). Patient sera from D20 (advanced periodontitis) did not react with this 27 kDa protein suggesting that antibodies directed toward the 27 kDa adhesin may have provided protection against peridontitis in patient H10 and the immunoprotected mice.

Epitope Mapping Analysis

Twenty overlapping 13 mer peptides (overlay by 6 and offset by 7 residues) corresponding to the N-terminal 148 residues of the PrtR27 were synthesised by Chiron Technologies (Melbourne, Australia) using the multipin peptide synthesis system. The sequence of the N-terminal 148 residues of the PrtR27 adhesin is as follows:
ANEAKVVLAADNVWDGNTGYQFLL-
DADHNTFGSVIPATGPLFTGTAS SDLYSANFESLI-
PANADPVVTTQNIIVTGQGEVVIPGGVY-
DYCITNPEPASGKM
WLAGDGGNQPARYDDFTFEAGKKYTFTM-
RRAGMGDGTDMEVEDDSPA (SEQ ID NO: 12).
The overlapping peptides synthesised were:
ANEAKVVLAADNV (SEQ ID NO:13)
LAADNVWDGNTGY (SEQ ID NO:14)
DGNTGYQFLLDAD (SEQ ID NO:15)
FLLDADHNTFGSV (SEQ ID NO:16)
NTFGSVIPATGPL (SEQ ID NO:17)
PATGPLFTGTASS (SEQ ID NO:18)
TGTASSDLYSANF (SEQ ID NO:19)
LYSANFESLIPAN (SEQ ID NO:20)
SLIPANADPVVTT (SEQ ID NO:21)
DPVVTTQNIIVTG (SEQ ID NO:22)
NIIVTGQGEVVIP (SEQ ID NO:23)
GEVVIPGGVYDYC (SEQ ID NO:24)
TNPEPASGKMWIA (SEQ ID NO:25)
GKMWIAGDGGNQP (SEQ ID NO:26)
DGGNQPARYDDFT (SEQ ID NO:27)

RYDDFTFEAGKKY (SEQ ID NO:28)
EAGKKYTFTMRRA (SEQ ID NO:29)
FTMRRAGMGDGTD (SEQ ID NO:30)
MGDGTDMEVEDDS (SEQ ID NO:31)
DGTDMEVEDDSPA (SEQ ID NO:32).

Epitope mapping of the pin-bound peptides was carried out by ELISA as per Chiron Technologies instructions using the human and mouse proteinase antisera at a dilution of 1:1000 in 1% w/v non-fat skim milk powder in 0.1M phosphate buffered saline, pH 7.4, containing 0.1% v/v Tween 20. The bound antibody was detected by incubating the peptide-PINS with 0.4 mM 3,3',5,5'-tetramethylbenzidine in 0.1M sodium acetate/citric acid buffer containing 0.004% v/v $H_2O_2$. Colour development was stopped by the addition of 2M $H_2SO_4$. Optical density (O.D.) was measured at 450 nm using a BioRad microplate reader model 450.

Figure 6:
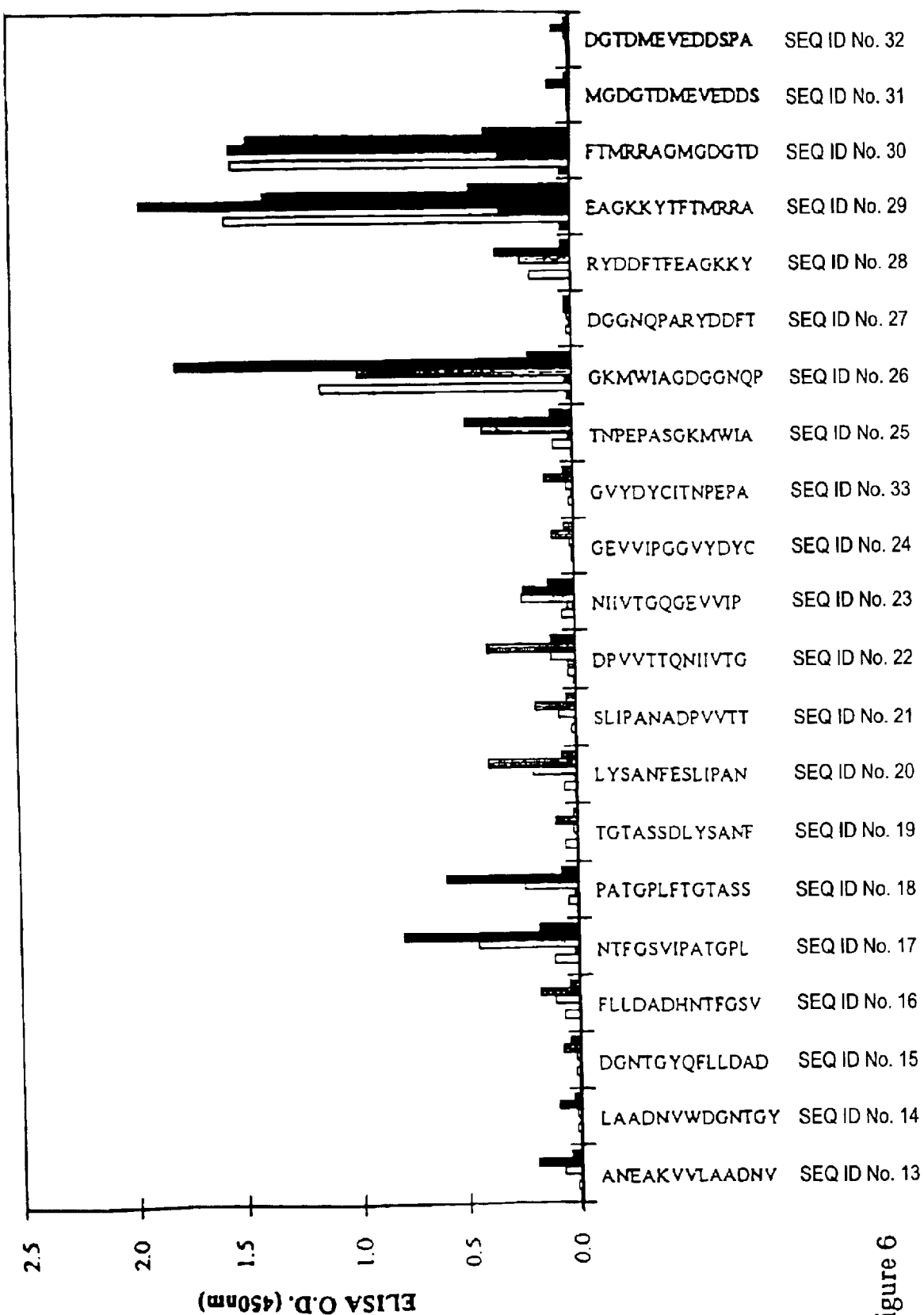
FIG. 6: Serum IgG antibody responses assessed by ELISA to Porphyromonas gingivalis PrtR-27 overlapping peptides (SEQ ID NOs:13–24, 33, and 25–32, respectively, from origin). Twenty one PIN-bound peptides were probed with normal mouse sera (■), protective mouse sera (□), normal human serum (■), patient D24 sera (■), patient H10 sera (■) and patient D20 sera (■). ELISAs were developed as per Example 1.
Figure 7:
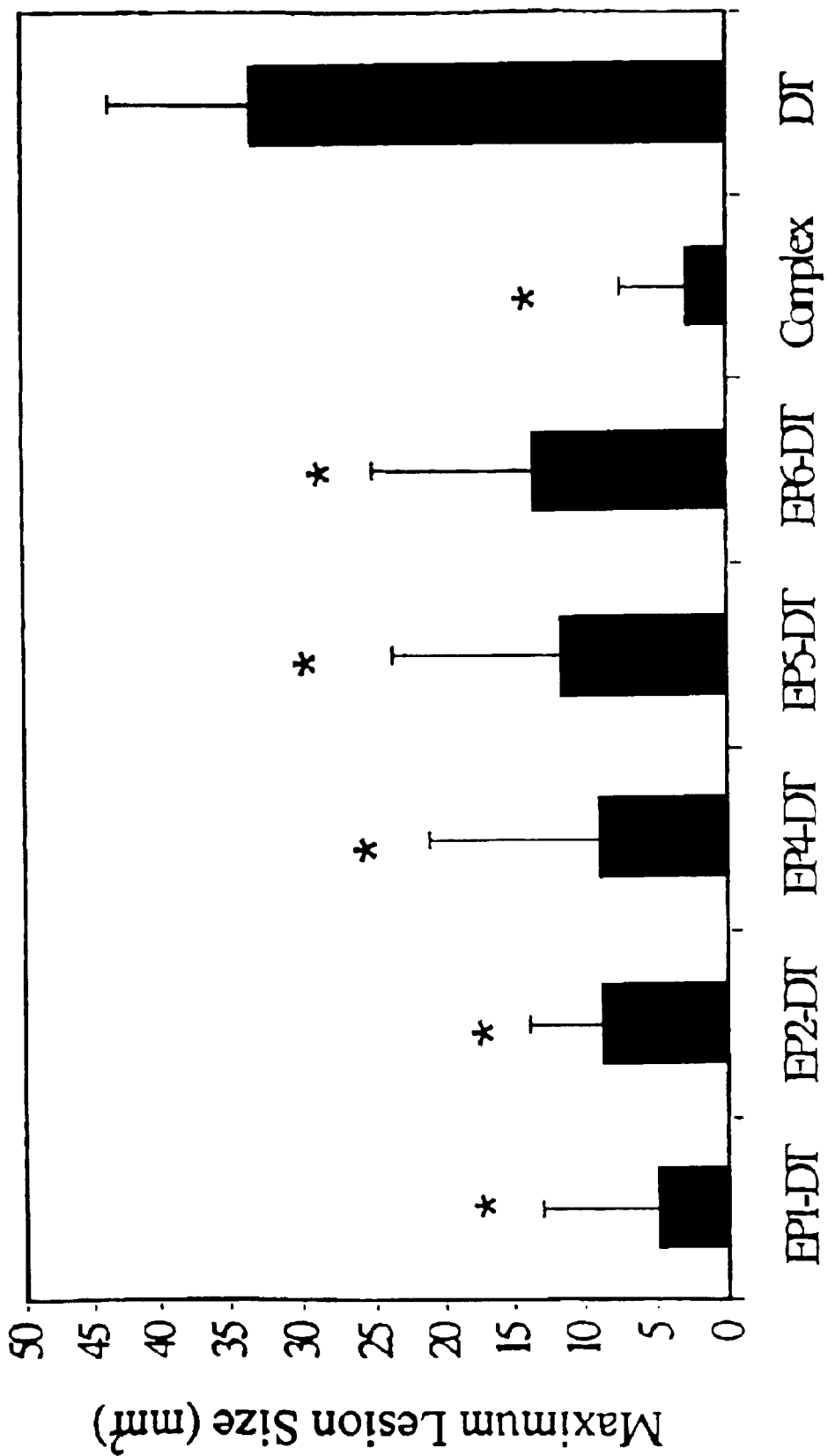
FIG. 7: Maximum lesion size of mice immunised with peptide-DT conjugates. BALB/c mice were immunised (s.c) with the peptide-DT conjugates (50 µg) administered in IFA for the primary and secondary doses and challenged (s.c.) 12 days after the second dose with P. gingivalis strain ATCC 33277 ($7.5×10^8$ viable cells). Animals were monitored over a 14 day period for weight loss and lesion size. Data was analysed using Kruskell-Wallis rank sum test and Mann-Whitney U-Wilcoxon rank sum test with a Bonferroni correction. *=$P \leq 0.005$, ns=not significant.

Antisera from D20, D24, H10 and the protective mouse sera were used to epitope map the N-terminal 148 residues of the PrtR27 adhesin using the PIN-bound overlapping peptides. FIG. 6 clearly shows four regions which bind antibody and have the sequences:
FLLDADHNTFGSVIPATGPLFTGTASS (SEQ ID NO:1)
LYSANFESLIPANADPVVTTQNIIVTG (SEQ ID NO:2)
TNPEPASGKMWIAGDGGNQP (SEQ ID NO:4)
RYDDFTFEAGKKYTFTMRRAGMGDGTD (SEQ ID NO:5)
The last two epitopes are part of a continuous sequence of the PrtR27 adhesin
TNPEPASGKMWIAGDGGNQPARYDDFTFEAGKKYTFTMRRAGMGDGTD (SEQ ID NO:7).

These protective epitope sequences of the PrtR27 adhesin are also found in the PrtK39 adhesin and the PrtR44 adhesin of the PrtR-PrtK proteinase-adhesin complex which explains the bands at 44, 39, and 27 kDa in the Western blot of the complex using the protective mouse sera. The PrtK39 sequence homologous to the PrtR27 protective epitope is LYSANFEYLIPANADPVVTTQNIIVTG (SEQ ID NO:3). The PrtR44 sequence homologous to the PrtR27 protective epitope is DDYVFEAGKKYHFLMKKMGSGDGTE (SEQ ID NO:6).

These sequences incorporated into a peptide construct or peptide protein conjugate therefore could form the basis of an immunogen to provide protection against periodontitis.

(ii) Synthesis of Peptide Antigens and Multiple Constructs

The peptides of Table 1 (EP1–EP7) can be synthesized using standard Fmoc or tBoc synthesis strategies and multipeptide constructs can be synthesized using the strategies outlined in FIGS. 1–5.

(iii) Preparation of Antibodies

Serum antibodies can be obtained by immunising horses, rabbits, sheep or dairy cows.

Immunizations can be carried out using standard procedures. The initial immunisation is usually with a mixture of the antigen and Freund's incomplete adjuvant. The antibodies can be recovered from the animals serum or milk using standard procedures.

EXAMPLE 2
Methods for Using Antigen Peptides in Diagnostic Immunoassays.

The *P. gingivalis* peptide antigens described herein can be synthesized for use as immunogens in vaccine formulations; and as antigens for diagnostic assays of for generating *P. gingivalis*-specific antisera of therapeutic and/or diagnostic value.

The peptides disclosed in Table 1 can be synthesized individually or chemically-linked using the strategies of FIGS. 1–5. The peptides can be synthesized using one of the several methods of peptide synthesis known in the art including standard solid phase peptide synthesis using ter-tbutyloxycarbonyl amino acids (Mitchell et al., 1978, *J. Org. Chem.* 43:2845–2852), using 9-fluorenylmethyloxycarbonyl amino acids on a polyamide support (Dryland et al., 1986, *J. Chem. So. Perkin Trans.* I, 125–137); by pepscan synthesis (Geysen et al., 1987, *J. Immunol. Methods* 03:259; 1984, *Proc. Natl. Acad. Sci. USA* 81:3998); or by standard liquid phase peptide synthesis. Modification of the peptides or oligopeptides, such as by deletion and substitution of amino acids (and including extensions and additions to amino acids) and in other ways, may be made so as to not substantially detract from the immunological properties of the peptide or oligopeptide. In particular, the amino acid sequences of the antigens described herein, may be altered by replacing one or more amino acids with functionally equivalent amino acids resulting in an alteration which is silent in terms of an observed difference in the physico-chemical behaviour of the peptide, or oligopeptide or chimera. Functionally equivalent amino acids are known in the art as amino acids which are related and/or have similar polarity or charge. Thus, an amino acid sequence which is substantially that of the amino acid sequences depicted in the Sequence Listing herein, refers to an amino acid sequence that contains substitutions with functionally equivalent amino acids without changing the primary biological function of the peptide, oligopeptide or chimera.

Purified synthetic peptides may be used as antigens in immunoassays for the detection of *P. gingivalis*-specific antisera present in the body fluid of an individual suspected of having an infection caused by *P. gingivalis*. The detection of antigens or related peptides in immunoassays, includes any immunoassay known in the art including, but not limited to, radioimmunoassay, enzyme-linked immunosorbent assay (ELISA), "sandwich" assay, precipitin reaction, agglutination assay, fluorescent immunoassay, and chemiluminescence-based immunoassay.

EXAMPLE 3
Synthesis of Protective Epitopes and Testing in a Murine Lesion Model.

The following peptides representative of the protective epitopes listed in Table 4 were synthesized, conjugated and tested in the murine lesion model.

TABLE 4

Origin and amino acid sequence of synthesised peptides

| Origin | Amino acid sequence [single letter code] | Abbreviatio |
|---|---|---|
| Protective Peptide Epitopes | | |
| PrtK39 (531–557) | FLLDADHNTFGSVIPATGPLFTGTASS (SEQ ID NO:1) | EP1 |
| PrtK39 (559–585) | LYSANFESLIPANADPVVTTQNIIVTG (SEQ ID NO:2) | EP2 |
| PrtK39 (601–620) | TNPEPASGKMWIAGDGGNQP (SEQ ID NO:4) | EP4 |
| PrtK39 (622–648) | RYDDFTFEAGKKYTFTMRRAGMGDGTD (SEQ ID NO:5) | EP5 |
| PrtR44 (604–627) | DDYVFEAGKKYHFLMKKMGSGDGTE (SEQ ID NO:6) | EP6 |

(i) Materials

Unless otherwise stated chemicals were of peptide synthesis grade or its equivalent. O-Benzotriazole-N,N,N',N'- tetramethyluronium hexafluorophosphate (HBTU), 1hydroxybenzotriazole (HOBt), diisopropylethylamine (DIPEA), N,N-dimethylformamide (DMF), piperidine, trifluoroacetic acid (TFA) and 9-fluorenylmethoxycarbonyl (Fmoc) protected amino acids were obtained from Auspep Pty Ltd (Melbourne, Australia). Triisopropylsilane (TIPS) and ethanedithiol (EDT) were obtained from Aldrich (New South Wales, Australia). 1,8-diazabicyclo[5.4.0]undec-7-ene (DBU) was obtained from Sigma Chemical Company (New South Wales, Australia). Phenol and diethyl ether was obtained from BDH (Poole, UK).

(ii) Solid-Phase Peptide Synthesis

Peptides were synthesized manually or usinga 431A ABI peptide synthesiser. Standard solid-phase peptide synthesis protocols for Fmoc chemistry were used throughout. Peptides were assembled as the carboxyamide form using Fmoc-Pal-Peg-PS resin (PerSeptive Biosystems Inc., Framingham, Mass.). Coupling was accomplished with HBTU/HOBt activation using 4 equiv of Fmoc-amino acid and 6 equiv of DIPEA. The Fmoc group was removed by 2% v/v DBU in DMF containing 2% v/v piperidine. Cleavage of peptides from the resin support was performed using TFA:phenol:TIPS:EDT:water (92:2:2:2:2) cleavage cocktail for 2.5 hours or 4 hours depending on the arginine content of the peptide. After cleavage the resin was removed by filtration and the filtrate concentrated to approximately 1 mL under a stream of nitrogen. After the peptide products were precipitated in cold ether, they were centrifuged and washed three times. The peptide precipitate was then dissolved in 5 to 10 mL of water containing 0.1% v/v TFA and insoluble residue removed by centrifugation.

(iii) Synthesis of S-Acetylmercaptoacetic Acid Peptides

Resins bearing peptides were swollen in DMF and the N-terminal Fmoc group removed by 2% v/v DBU in DMF containing 2% v/v piperidine. S-Acetylmercaptoacetic acid (SAMA) group was introduced onto the N-terminal amino group using 5 equiv of SAMA-OPfp and 5 equiv of HOBt. The reaction was monitored by the trinitrobenzene sulphonic acid (TNBSA) test. When a negative TNBSA test was returned the resin was washed (5×DMF, 3×DCM and 3×diethyl ether). The resin was dried under vacuum and the SAMA-peptides cleaved from the resin support as described above.

(iv) Peptide Purification.

Purification of synthesized peptides was performed using a Brownlee C18 Aquapore ODS column (250×100 mm) installed in a Waters HPLC system. Chromatograms were developed at a flow rate of 5 mL/min using 0.1% v/v TFA in water (solvent A) and 0.1% v/v TFA in 90% aqueous acetonitrile (solvent B) as the limit buffer. Peptides were eluted with a gradient of 10–30% solvent B formed over 40 min. Analytical HPLC was carried out using a Brownlee C8 Aquapore RP-300 column (220×4.6 mm) installed in a Applied Biosystems HPLC system. Chromatograms were developed using solvent A and solvent B at a flow rate of 1 mL/min and a 0–100% linear gradient of solvent B formed over 30 min. Material eluted from the columns was detected by determining the absorbance at 214 nm. Peptide fractions were pooled and lyophilised. Peptides were analysed by mass spectrometry using a PerSeptive Biosystems Voyager DE MALDI-TOF.

(v) Conjugation of SAMA-Peptides to Diphtheria Toxoid

Diphtheria toxoid (DT) was obtained from CSL Limited, Melbourne, Australia which contained 9 equivalent amino groups per 62 kDa molecule. To a solution containing 10 mg/mL of DT in phosphate-buffered saline (0.1M sodium phosphate, 0.9% NaCl; pH 7.4) was added 0.1 mL of a 1% w/v solution m-maleimido benzoyl-N-hydroxysuccinimide ester (MBS) in DMF. After 30 mins unreacted MBS was removed and MBS modified DT collected by gel filtration using a PD10 column (Pharmacia, NSW, Australia) equilibrated in conjugation buffer (0.1M sodium phosphate, 5 mM EDTA; pH 6.0). Purified SAMA-peptide (1.3 $\mu$mole) was dissolved in 200 $\mu$L 6M guanidine HCl containing 0.5M Tris; 2 mM EDTA, pH6 and diluted with 800 $\mu$L MilliQ water and deprotected in-situ by addition of 25 $\mu$L of 2M NH2OH (40 equiv) dissolved in MilliQ water. The collected MBS-DT was immediately reacted with deprotected SAMA-peptide and stirred for one hour at room temperature. The peptide-DT conjugate was separated from unreacted peptide by gel filtration using a PD10 column equilibrated in PBS pH 7.4 and lyophilised. The reaction was monitored using the Ellmans test. The conjugation yields of SAMA-peptides to MBS-DT ranged from 34% to 45% indicating that 3 to 4 peptides were coupled per DT molecule.

(vi) Immunization and Murine Lesion Model Protocols.

BALB/c mice 6–8 weeks old were immunised subcutaneously with either 50 μg of the peptide-DT conjugate, 50 μg of DT or 25 μg of the PrtR-PrtK proteinase adhesin complex from *P. gingivalis* strain W50 emulsifiedin complete Freund's adjuvant (CFA). After 30 days the mice were injected subcutaneously with antigen (either 50 μg of the peptide-DT conjugate, 50 μg of DT or 25 μg of the PrtR-PrtK proteinase adhesin complex from *P. gingivalis* strain W50) emulsified in incomplete Freund's adjuvant (IFA) and then bled from the retrobulbar plexus 12 days later. All mice were challenged with $7.5\times10^9$ cells of *P. gingivalis* (200 μL) by subcutaneous injection in the abdomen and weighed and lesion size measured over 10 days. Lesion sizes are expressed as mm2 and were statistically analysed using a Kruskal-Wallis one-way ANOVA and Mann-Whitney U-Wilcoxon rank sum test. A Bonferroni correction of type 1 error was used when comparing peptide groups with the control (DT) group.

FIG. 7 shows maximum lesion size that developed for each group. Statistical analysis of the data indicated that mice immunised with either EP1-DT, EP2-DT, EP4-DT, EP5-DT, EP6-DT and the complex had significantly ($p<0.005$) smaller lesions than that of the control group immunised with DT alone.

The results demonstrate the efficacy of the EP protective peptides when used as immunogens in preventing challenge with *P. gingivalis* in the murine lesion model.

EXAMPLE 4

Methods and Compounds for Vaccine Formulations Related to Synthetic Peptide Antigens and Multipeptide Constructs.

This embodiment of the present invention is to provide peptide antigens of Table 1 to be used as immunogens in a prophylactic and/or therapeutic vaccine for active immunization to protect against or treat infections caused by *P. gingivalis*. For vaccine purposes, an antigen of *P. gingivalis* comprising a synthetic peptide construct should be immunogenic, and induce functional antibodies directed to one or more surface-exposed epitopes on intact bacteria, wherein the epitope(s) are conserved amongst strains of *P. gingivalis.*

In one illustration of the invention, the dipeptide EP4–EP5 construct having the properties desirable of a vaccine antigen, the dipeptide construct can be synthesized using the method described herein in FIGS. 1–5.

The synthetic peptide is included as the relevant immunogenic material in the vaccine formulation, and in therapeutically effective amounts, to induce an immune response. Many methods are known for the introduction of a vaccine formulation into the human or animal to be vaccinated.

These include, but are not limited to, intradermal, intramuscular, intraperitoneal, intravenous, subcutaneous, ocular, intranasal, and oral administration. The vaccine may further comprise a physiological carrier such as a solution, a polymer or liposomes; and an adjuvant, or a combination thereof.

Various adjuvants are used in conjunction with vaccine formulations. The adjuvants aid by modulating the immune response and in attaining a more durable and higher level of immunity using smaller amounts of vaccine antigen or fewer doses than if the vaccine antigen were administered alone. Examples of adjuvants include incomplete Freund's adjuvants (ISA), Adjuvant 65 (containing peanut oil, mannide monooleate and aluminum monostearate), oil emulsions, Ribi adjuvant, the pluronic polyols, polyamines, Avridine, Quil A, saponin, MPL, QS-21, and mineral gels such as aluminum hydroxide, aluminum phosphate, etc.

Another embodiment of this mode of the invention involves the production of antigen-specific amino acid sequences as a hapten, i.e. a molecule which cannot by itself elicit an immune response. In such case, the hapten may be covalently bound to a carrier or other immunogenic molecule which will confer immunogenicity to the coupled hapten when exposed to the immune system. Thus, such a antigen-specific hapten linked to a carrier molecule may be the immunogen in a vaccine formulation.

As an alternative to active immunization, immunization may be passive, i.e. immunization comprising administration of purified immunoglobulin containing antibody against synthetic peptides.

EXAMPLE 5

The following is a proposed toothpaste formulation containing anti-peptide antibodies.

EXAMPLE 5
The following is a proposed toothpaste formulation containing anti-peptide antibodies.

| Ingredient | % w/w |
| --- | --- |
| Dicalcium phosphate dihydrate | 50.0 |
| Glycerol | 20.0 |
| Sodium carboxymethyl cellulose | 1.0 |
| Sodium lauryl sulphate | 1.5 |
| Sodium lauroyl sarconisate | 0.5 |
| Flavour | 1.0 |
| Sodium saccharin | 0.1 |
| Chlorhexidine gluconate | 0.01 |
| Dextranase | 0.01 |
| Goat serum containing anti-peptide Abs | 0.2 |
| Water | balance |

EXAMPLE 6

The following is a proposed toothpaste formulation.

EXAMPLE 6
The following is a proposed toothpaste formulation.

| Ingredient | % w/w |
| --- | --- |
| Dicalcium phosphate dihydrate | 50.0 |
| Sorbitol | 10.0 |
| Glycerol | 10.0 |
| Sodium carboxymethyl cellulose | 1.0 |
| Sodium lauryl sulphate | 1.5 |
| Sodium lauroyl sarconisate | 0.5 |
| Flavour | 1.0 |
| Sodium saccharin | 0.1 |
| Sodium monofluorophosphate | 0.3 |
| Chlorhexidine gluconate | 0.01 |
| Dextranase | 0.01 |
| Bovine serum containing anti-peptide Abs | 0.2 |
| Water | balance |

EXAMPLE 7

The following is a proposed toothpaste formulation.

EXAMPLE 7
The following is a proposed toothpaste formulation.

| Ingredient | % w/w |
| --- | --- |
| Dicalcium phosphate dihydrate | 50.0 |
| Sorbitol | 10.0 |
| Glycerol | 10.0 |
| Sodium carboxymethyl cellulose | 1.0 |
| Lauroyl diethanolamide | 1.0 |
| Sucrose monolaurate | 2.0 |
| Flavour | 1.0 |
| Sodium saccharin | 0.1 |
| Sodium monofluorophosphate | 0.3 |
| Chlorhexidine gluconate | 01 |
| Dextranase | 0.01 |
| Bovine milk Ig containing anti-peptide Abs | 0.1 |
| Water | balance |

EXAMPLE 8

The following is a proposed toothpaste formulation.

EXAMPLE 8
The following is a proposed toothpaste formulation.

| Ingredient | % w/w |
| --- | --- |
| Sorbitol | 22.0 |
| Irish moss | 1.0 |
| Sodium Hydroxide (50%) | 1.0 |
| Gantrez | 19.0 |
| Water (deionised) | 2.69 |
| Sodium Monofluorophosphate | 0.76 |
| Sodium saccharine | 0.3 |
| Pyrophosphate | 2.0 |
| Hydrated alumina | 48.0 |
| Flavour oil | 0.95 |
| anti-peptide mouse monoclonal | 0.3 |
| sodium lauryl sulphate | 2.00 |

EXAMPLE 9

The following is a proposed liquid toothpaste formulation.

EXAMPLE 9
The following is a proposed liquid toothpaste formulation.

| Ingredient | % w/w |
| --- | --- |
| Sodium polyacrylate | 50.0 |
| Sorbitol | 10.0 |

EXAMPLE 9
The following is a proposed liquid toothpaste formulation.

| Ingredient | % w/w |
|---|---|
| Glycerol | 20.0 |
| Flavour | 1.0 |
| Sodium saccharin | 0.1 |
| Sodium monofluorophosphate | 0.3 |
| Chlorhexidine gluconate | 0.01 |
| Ethanol | 3.0 |
| Equine Ig containing anti-peptide Ab | 0.2 |
| Linolic acid | 0.05 |
| Water | balance |

EXAMPLE 10
The following is a proposed mouthash formulation.

EXAMPLE 10
The following is a proposed mouthwash formulation.

| Ingredient | % w/w |
|---|---|
| Ethanol | 20.0 |
| Flavour | 1.0 |
| Sodium saccharin | 0.1 |
| Sodium monofluorophosphate | 0.3 |
| Chlorhexidine gluconate | 0.01 |
| Lauroyl diethanolamide | 0.3 |
| Rabbit Ig containing anti-peptide-Ab | 0.2 |
| Water | balance |

EXAMPLE 11
The following is a proposed mouthwash formulation.

EXAMPLE 11
The following is a proposed mouthwash formulation.

| Ingredient | % w/w |
|---|---|
| Gantrez S-97 | 2.5 |
| Glycerine | 10.0 |
| Flavour oil | 0.4 |
| Sodium monofluorophosphate | 0.05 |
| Chlorhexidine gluconate | 0.01 |
| Lauroyl diethanolamide | 0.2 |
| Mouse anti-peptide monoclonal | 0.3 |
| Water | balance |

EXAMPLE 12
The following is a proposed lozenge formulation.

EXAMPLE 12
The following is a proposed lozenge formulation.

| Ingredient | % w/w |
|---|---|
| Sugar | 75–80 |
| Corn syrup | 1–20 |
| Flavour oil | 1–2 |
| NaF | 0.01–0.05 |
| Mouse anti-peptide monoclonal | 0.3 |
| Mg stearate | 1–5 |
| Water | balance |

EXAMPLE 13
The following is a proposed gingival massage cream formulation.

EXAMPLE 13
The following is a proposed gingival massage cream formulation.

| Ingredient | % w/w |
|---|---|
| White petrolatum | 8.0 |
| Propylene glycol | 4.0 |
| Stearyl alcohol | 8.0 |
| Polyethylene Glycol 4000 | 25.0 |
| Polyethylene Glycol 400 | 37.0 |
| Sucrose monostearate | 0.5 |
| Chlorohexidine gluconate | 0.1 |
| Mouse anti-peptide monoclonal | 0.3 |
| Water | balance |

EXAMPLE 14
The following is a proposed chewing gum formulation.

EXAMPLE 14
The following is a proposed chewing gum formulation.

| Ingredient | % w/w |
|---|---|
| Gum base | 30.0 |
| Calcium carbonate | 2.0 |
| Crystalline sorbitol | 53.0 |
| Glycerine | 0.5 |
| Flavour oil | 0.1 |
| Mouse anti-peptide monoclonals | 0.3 |
| Water | balance |

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

Alexander, J., Sidney, J., Southwood, S., et al (1994). Development of high potentcy universal DR-restricted helper epitopes by modification of high affinity DR-blocking peptides. *Immunity* 1: 751–761.

Canne, L. E., Ferre-D'Amare, A. R., Burley, S. K., and Kent, S. B. H. (1995). Total chemical synthesis of a unique transcription factor-related protein: cMyc-Max. *J. A. Chem. Soc.* 117: 2998–3001.

Druland, et. al. (1986). *J. Chem. Soc. Perkin Trans.* 1: 125–137.

Duncan, R., and Kopececk, J. (1980). Degradation of side chains of N-(2-hydroxypropyl)methacrylamide copolymers by lysosomal enzymes. *Biochem. Biophys. Res. Commun.* 94: 284–290.

Geysen, H. M., Meleon, R. H., and Barteling, S. J. (1984). Use of peptide synthesis to probe viral antigens for epitopes to a resolution of a single amino acid. *Proc. Natl. Acad. Sci. USA.* 81: 3998.

Geysen, H. M., Rodda, S. J., Mason, T. J., et al. (1987). Strategies for epitope mapping using peptide synthesis. *J. Immunol. Methods.* 102: 259.

Hammet, J., Valsasnini, P., Tolba, K., Bolin, D., Higelin, J., Takacs, B., and Sinigaglia, F. (1993). Promiscuous and allele-specific anchors in HLA-DR-binding peptides. *Cell* 74: 197–203.

Kaumaya, P. T. P., Kobs-Conrad, S., and DiGeorge, A. M. (1994). Synthetic peptide vaccines: Misconceptions and problems, strategies and prospects *Innovation and Perspectives in Solid Phase Synthesis*. R. Epton. Kingswinford, Mayflower: 279–292.

Kesavalu, L., Ebersole, J. L., Machen, R. L., Holt, S. C. (1992). *Porphyromonas gingivalis* virulence in mice: induction of immunity to bacterial components. *Infect. Immun.* 60: 1455–1464.

Liu, C. F. a. T., J. P. (1994). Peptide ligation strategy without use of protecting groups. *Proc. Natl. Acad. Sci. USA* 91: 6584–6588.

Lu, Y. A., Clavijo, P., Galantino, M., Shen. Z. Y., and Tam, J. P. (1991). Chemically unambiguous peptide immunogen: Preparation, orientation and antigenicity of purified peptide cinjugated to the multiple antigen peptide system. *Mol. Immunol.* 28(6): 623–630.

Mitchell., e. a. (1978). *J. Org. Chem.* 43: 2845–2852.

O'Brien-Simpson, N. M., Ede, N. J., Brown, L. E., Swan, J., and Jackson, D. C. (1997). Polymerisation of unprotected synthetic peptides: a view towards a synthetic peptide vaccines. *J. Am. Chem. Soc.* 117(6).

O'Sullivan, D., Arrhenius, T., Sidney, J., et al (1991). On the interaction of promiscuous antigenic peptides with different DR alleles. Indentification of common structural motifs. *J. Immunol* 147(8): 2663–2669.

Rose, K. (1994). Facile synthesis of homogeneous artificial proteins. *J. Am. Chem. Soc.* 116: 30–33.

Rose, J., Zeng, W., Regamey, P. O., Chernusheivich, I. V., Standing, K. G., and Gaertner, H. F. (1996). Natural peptides as building blocks for the synthesis of large protein-like molecules with hydrazone and oxime linkages. *Bioconjugate Chem.* 7(5): 552–556.

Shao, J., and Tam, J. P. (1995). *J. Am. Chem. Soc.* 11 7: 3893–3899.

Spetzler, J. C. a. T., J. P. (1994). A general approach for the synthesis of branched peptides for synthetic vaccines: Synthesis of multiple antigen peptides using unprotected segments. *Innovation and Perspectives in Solid Phase Synthesis*. R. Epton. Kingswinford, Mayflower: 293–300.

van Noort, J. M., and van der Drift, A. C. M. (1989). The selectivity of cathepsin D suggests an involvement of the enzyme in the generation of T-cell epitopes. *J. Biol. Chem:* 264(24): 14159–14164.

What is claimed is:

1. A composition for use in raising an immune response against *Porphyromonas gingivalis*, the composition comprising a suitable adjuvant and/or acceptable carrier or excipient and at least one peptide of not more than 50 amino acids which peptide includes at least one *P. gingivalis* epitope, or multimers of said peptide, the at least one *P. gingivalis* epitope comprising the sequence RYDDFTFEAGKKYTFTMRRAGMGDGTD (SEQ ID NO:5).

2. A composition as claimed in claim 1 in which the at least one peptide comprises the sequence TNPEPASGKMWLAGDGGNQPARYDDFTFEAGKKYTFTMRRAGMGDGTD (SEQ ID NO:7).

3. A composition as claimed in claim 1 in which the at least one peptide is RYDDFTFEAGKKYTFTMRRAGMGDGTD (SEQ ID NO:5).

4. A composition as claimed in claim 1 in which the at least one peptide is TNPEPASGKMWIAGDGGNQPARYDDFTFEAGKKYTFTMRRAGMGDGTD (SEQ ID NO:7).

5. A composition as claimed in claim 1 which comprises more than one peptide.

6. A composition in claim 5 in which the peptides are in multimeric form(s).

* * * * *

SEQUENCE LISTING

```
<160> NUMBER OF SEQ ID NOS: 33

<210> SEQ ID NO 1
<211> LENGTH: 27
<212> TYPE: PRT
<213> ORGANISM: Porphyromonas gingivalis

<400> SEQUENCE: 1

Phe Leu Leu Asp Ala Asp His Asn Thr Phe Gly Ser Val Ile Pro Ala
 1               5                  10                  15

Thr Gly Pro Leu Phe Thr Gly Thr Ala Ser Ser
             20                  25

<210> SEQ ID NO 2
<211> LENGTH: 27
<212> TYPE: PRT
<213> ORGANISM: Porphyromonas gingivalis

<400> SEQUENCE: 2

Leu Tyr Ser Ala Asn Phe Glu Ser Leu Ile Pro Ala Asn Ala Asp Pro
 1               5                  10                  15

Val Val Thr Thr Gln Asn Ile Ile Val Thr Gly
             20                  25

<210> SEQ ID NO 3
<211> LENGTH: 27
<212> TYPE: PRT
<213> ORGANISM: Porphyromonas gingivalis

<400> SEQUENCE: 3

Leu Tyr Ser Ala Asn Phe Glu Tyr Leu Ile Pro Ala Asn Ala Asp Pro
```

```
                1               5              10              15
Val Val Thr Thr Gln Asn Ile Ile Val Thr Gly
            20              25
```

<210> SEQ ID NO 4
<211> LENGTH: 20
<212> TYPE: PRT
<213> ORGANISM: Porphyromonas gingivalis

<400> SEQUENCE: 4

```
Thr Asn Pro Glu Pro Ala Ser Gly Lys Met Trp Ile Ala Gly Asp Gly
 1               5                  10                  15

Gly Asn Gln Pro
            20
```

<210> SEQ ID NO 5
<211> LENGTH: 27
<212> TYPE: PRT
<213> ORGANISM: Porphyromonas gingivalis

<400> SEQUENCE: 5

```
Arg Tyr Asp Asp Phe Thr Phe Glu Ala Gly Lys Lys Tyr Thr Phe Thr
 1               5                  10                  15

Met Arg Arg Ala Gly Met Gly Asp Gly Thr Asp
            20                  25
```

<210> SEQ ID NO 6
<211> LENGTH: 25
<212> TYPE: PRT
<213> ORGANISM: Porphyromonas gingivalis

<400> SEQUENCE: 6

```
Asp Asp Tyr Val Phe Glu Ala Gly Lys Lys Tyr His Phe Leu Met Lys
 1               5                  10                  15

Lys Met Gly Ser Gly Asp Gly Thr Glu
            20                  25
```

<210> SEQ ID NO 7
<211> LENGTH: 48
<212> TYPE: PRT
<213> ORGANISM: Porphyromonas gingivalis

<400> SEQUENCE: 7

```
Thr Asn Pro Glu Pro Ala Ser Gly Lys Met Trp Ile Ala Gly Asp Gly
 1               5                  10                  15

Gly Asn Gln Pro Ala Arg Tyr Asp Asp Phe Thr Phe Glu Ala Gly Lys
            20                  25                  30

Lys Tyr Thr Phe Thr Met Arg Arg Ala Gly Met Gly Asp Gly Thr Asp
        35                  40                  45
```

<210> SEQ ID NO 8
<211> LENGTH: 13
<212> TYPE: PRT
<213> ORGANISM: Porphyromonas gingivalis

<400> SEQUENCE: 8

```
Asn Thr Phe Gly Ser Val Ile Pro Ala Thr Gly Pro Leu
 1               5                  10
```

<210> SEQ ID NO 9
<211> LENGTH: 12
<212> TYPE: PRT

```
<213> ORGANISM: Porphyromonas gingivalis

<400> SEQUENCE: 9

Pro Ala Ser Gly Lys Met Trp Ile Ala Gly Asp Gly
  1               5                  10

<210> SEQ ID NO 11
<211> LENGTH: 13
<212> TYPE: PRT
<213> ORGANISM: Porphyromonas gingivalis

<400> SEQUENCE: 10

Glu Ala Gly Lys Lys Tyr Thr Phe Thr Met Arg Arg Ala
  1               5                  10

<210> SEQ ID NO 11
<211> LENGTH: 13
<212> TYPE: PRT
<213> ORGANISM: Porphyromonas gingivalis

<400> SEQUENCE: 11

Glu Ala Gly Lys Lys Tyr His Phe Leu Met Lys Lys Met
  1               5                  10

<210> SEQ ID NO 12
<211> LENGTH: 148
<212> TYPE: PRT
<213> ORGANISM: Porphyromonas gingivalis

<400> SEQUENCE: 12

Ala Asn Glu Ala Lys Val Val Leu Ala Ala Asp Asn Val Trp Asp Gly
  1               5                  10                  15

Asn Thr Gly Tyr Gln Phe Leu Leu Asp Ala Asp His Asn Thr Phe Gly
                 20                  25                  30

Ser Val Ile Pro Ala Thr Gly Pro Leu Phe Thr Gly Thr Ala Ser Ser
             35                  40                  45

Asp Leu Tyr Ser Ala Asn Phe Glu Ser Leu Ile Pro Ala Asn Ala Asp
         50                  55                  60

Pro Val Thr Thr Gln Asn Ile Ile Val Thr Gly Gln Gly Glu Val
 65                  70                  75                  80

Val Ile Pro Gly Gly Val Tyr Asp Tyr Cys Ile Thr Asn Pro Glu Pro
                 85                  90                  95

Ala Ser Gly Lys Met Trp Ile Ala Gly Asp Gly Gly Asn Gln Pro Ala
            100                 105                 110

Arg Tyr Asp Asp Phe Thr Phe Glu Ala Gly Lys Lys Tyr Thr Phe Thr
        115                 120                 125

Met Arg Arg Ala Gly Met Gly Asp Gly Thr Asp Met Glu Val Glu Asp
    130                 135                 140

Asp Ser Pro Ala
145

<210> SEQ ID NO 13
<211> LENGTH: 13
<212> TYPE: PRT
<213> ORGANISM: Porphyromonas gingivalis

<400> SEQUENCE: 13

Ala Asn Glu Ala Lys Val Val Leu Ala Ala Asp Asn Val
  1               5                  10
```

```
<210> SEQ ID NO 14
<211> LENGTH: 13
<212> TYPE: PRT
<213> ORGANISM: Porphyromonas gingivalis

<400> SEQUENCE: 14

Leu Ala Ala Asp Asn Val Trp Asp Gly Asn Thr Gly Tyr
 1               5                  10

<210> SEQ ID NO 15
<211> LENGTH: 13
<212> TYPE: PRT
<213> ORGANISM: Porphyromonas gingivalis

<400> SEQUENCE: 15

Asp Gly Asn Thr Gly Tyr Gln Phe Leu Leu Asp Ala Asp
 1               5                  10

<210> SEQ ID NO 16
<211> LENGTH: 13
<212> TYPE: PRT
<213> ORGANISM: Porphyromonas gingivalis

<400> SEQUENCE: 16

Phe Leu Leu Asp Ala Asp His Asn Thr Phe Gly Ser Val
 1               5                  10

<210> SEQ ID NO 17
<211> LENGTH: 13
<212> TYPE: PRT
<213> ORGANISM: Porphyromonas gingivalis

<400> SEQUENCE: 17

Asn Thr Phe Gly Ser Val Ile Pro Ala Thr Gly Pro Leu
 1               5                  10

<210> SEQ ID NO 18
<211> LENGTH: 13
<212> TYPE: PRT
<213> ORGANISM: Porphyromonas gingivalis

<400> SEQUENCE: 18

Pro Ala Thr Gly Pro Leu Phe Thr Gly Thr Ala Ser Ser
 1               5                  10

<210> SEQ ID NO 19
<211> LENGTH: 13
<212> TYPE: PRT
<213> ORGANISM: Porphyromonas gingivalis

<400> SEQUENCE: 19

Thr Gly Thr Ala Ser Ser Asp Leu Tyr Ser Ala Asn Phe
 1               5                  10

<210> SEQ ID NO 20
<211> LENGTH: 13
<212> TYPE: PRT
<213> ORGANISM: Porphyromonas gingivalis

<400> SEQUENCE: 20

Leu Tyr Ser Ala Asn Phe Glu Ser Leu Ile Pro Ala Asn
 1               5                  10

<210> SEQ ID NO 21
<211> LENGTH: 13
```

```
<212> TYPE: PRT
<213> ORGANISM: Porphyromonas gingivalis

<400> SEQUENCE: 21

Ser Leu Ile Pro Ala Asn Ala Asp Pro Val Thr Thr
 1               5                  10

<210> SEQ ID NO 22
<211> LENGTH: 13
<212> TYPE: PRT
<213> ORGANISM: Porphyromonas gingivalis

<400> SEQUENCE: 22

Asp Pro Val Val Thr Thr Gln Asn Ile Ile Val Thr Gly
 1               5                  10

<210> SEQ ID NO 23
<211> LENGTH: 13
<212> TYPE: PRT
<213> ORGANISM: Porphyromonas gingivalis

<400> SEQUENCE: 23

Asn Ile Ile Val Thr Gly Gln Gly Glu Val Val Ile Pro
 1               5                  10

<210> SEQ ID NO 24
<211> LENGTH: 13
<212> TYPE: PRT
<213> ORGANISM: Porphyromonas gingivalis

<400> SEQUENCE: 24

Gly Glu Val Val Ile Pro Gly Gly Val Tyr Asp Tyr Cys
 1               5                  10

<210> SEQ ID NO 25
<211> LENGTH: 13
<212> TYPE: PRT
<213> ORGANISM: Porphyromonas gingivalis

<400> SEQUENCE: 25

Thr Asn Pro Glu Pro Ala Ser Gly Lys Met Trp Ile Ala
 1               5                  10

<210> SEQ ID NO 26
<211> LENGTH: 13
<212> TYPE: PRT
<213> ORGANISM: Porphyromonas gingivalis

<400> SEQUENCE: 26

Gly Lys Met Trp Ile Ala Gly Asp Gly Gly Asn Gln Pro
 1               5                  10

<210> SEQ ID NO 27
<211> LENGTH: 13
<212> TYPE: PRT
<213> ORGANISM: Porphyromonas gingivalis

<400> SEQUENCE: 27

Asp Gly Gly Asn Gln Pro Ala Arg Tyr Asp Asp Phe Thr
 1               5                  10

<210> SEQ ID NO 28
<211> LENGTH: 13
<212> TYPE: PRT
<213> ORGANISM: Porphyromonas gingivalis
```

```
<400> SEQUENCE: 28

Arg Tyr Asp Asp Phe Thr Phe Glu Ala Gly Lys Lys Tyr
 1               5                  10

<210> SEQ ID NO 29
<211> LENGTH: 13
<212> TYPE: PRT
<213> ORGANISM: Porphyromonas gingivalis

<400> SEQUENCE: 29

Glu Ala Gly Lys Lys Tyr Thr Phe Thr Met Arg Arg Ala
 1               5                  10

<210> SEQ ID NO 30
<211> LENGTH: 13
<212> TYPE: PRT
<213> ORGANISM: Porphyromonas gingivalis

<400> SEQUENCE: 30

Phe Thr Met Arg Arg Ala Gly Met Gly Asp Gly Thr Asp
 1               5                  10

<210> SEQ ID NO 31
<211> LENGTH: 13
<212> TYPE: PRT
<213> ORGANISM: Porphyromonas gingivalis

<400> SEQUENCE: 31

Met Gly Asp Gly Thr Asp Met Glu Val Glu Asp Asp Ser
 1               5                  10

<210> SEQ ID NO 32
<211> LENGTH: 13
<212> TYPE: PRT
<213> ORGANISM: Porphyromonas gingivalis

<400> SEQUENCE: 32

Asp Gly Thr Asp Met Glu Val Glu Asp Asp Ser Pro Ala
 1               5                  10

<210> SEQ ID NO 33
<211> LENGTH: 12
<212> TYPE: PRT
<213> ORGANISM: Porphyromonas gingivalis

<400> SEQUENCE: 33

Gly Thr Asp Met Glu Val Glu Asp Asp Ser Pro Ala
 1               5                  10
```